(12) United States Patent
Inoue

(10) Patent No.: US 8,160,329 B2
(45) Date of Patent: Apr. 17, 2012

(54) MEDICAL IMAGE PROCESSING DEVICE AND MEDICAL IMAGE PROCESSING METHOD

(75) Inventor: Ryoko Inoue, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 585 days.

(21) Appl. No.: 12/366,116

(22) Filed: Feb. 5, 2009

(65) Prior Publication Data

US 2009/0196476 A1 Aug. 6, 2009

Related U.S. Application Data

(63) Continuation of application No. PCT/JP2007/063483, filed on Jul. 5, 2007.

(30) Foreign Application Priority Data

Aug. 8, 2006 (JP) ................................. 2006-216250

(51) Int. Cl.
*G06K 9/00* (2006.01)
(52) U.S. Cl. ....................................... 382/128; 382/132
(58) Field of Classification Search .................. 382/128, 382/131, 132, 162, 167
See application file for complete search history.

(56) References Cited

U.S. PATENT DOCUMENTS

| 6,297,044 | B1 | 10/2001 | Eisen et al. | |
|---|---|---|---|---|
| 7,747,055 | B1 * | 6/2010 | Vining et al. | 382/131 |
| 2005/0036668 | A1 * | 2/2005 | McLennan et al. | 382/128 |
| 2006/0257031 | A1 * | 11/2006 | Abramoff et al. | 382/224 |
| 2008/0260218 | A1 * | 10/2008 | Smith et al. | 382/128 |

FOREIGN PATENT DOCUMENTS

| JP | 2005-192880 | 7/2005 |
|---|---|---|
| WO | WO 02/073507 A2 | 9/2002 |

OTHER PUBLICATIONS

Extended Supplementary European Search Report dated Apr. 15, 2010.

* cited by examiner

*Primary Examiner* — Joseph Chang
*Assistant Examiner* — Jeffrey Shin
(74) *Attorney, Agent, or Firm* — Scully, Scott, Murphy & Presser, P.C.

(57) ABSTRACT

A medical image processing device of the present invention has an image dividing unit which divides an image into a plurality of regions, a feature value calculating unit which calculates a color tone feature value which is a feature value based on a color tone of the image in each of the plurality of regions, a first color tone reference value calculating unit which calculates a color tone reference value based on the color tone feature value which each of the plurality of regions has, a lesion detection reference calculating unit which properly calculates a lesion detection reference for detecting a lesion finding in accordance with the color tone reference value, and an image region detecting unit which detects a region in which an image of the lesion finding is picked up among the respective plurality of regions, based on the lesion detection reference and the color tone feature value which each of the plurality of regions has.

42 Claims, 15 Drawing Sheets

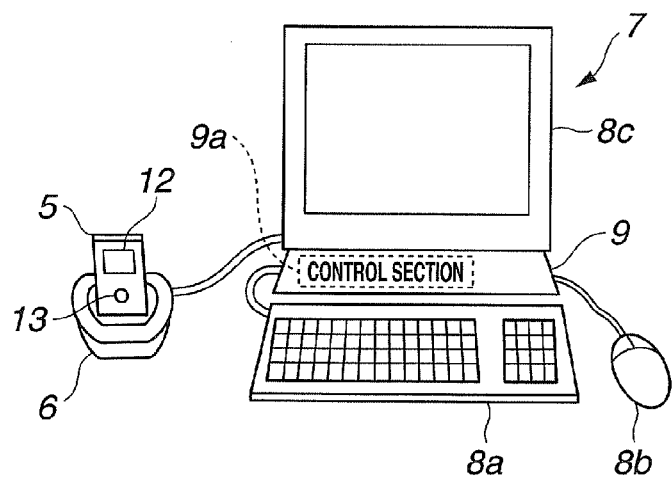
FIG.1
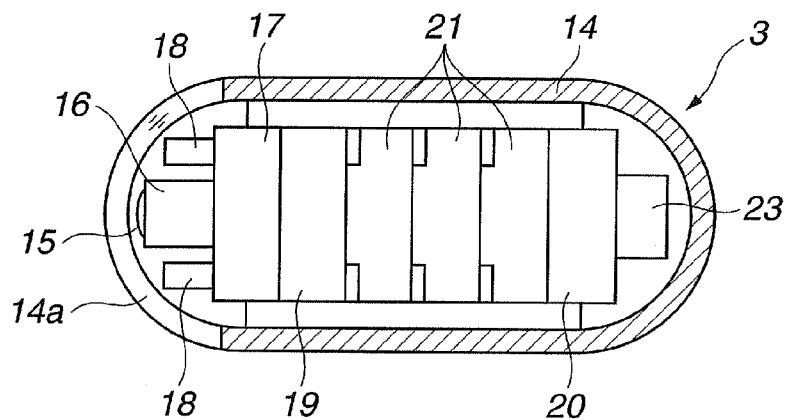
FIG.2
FIG.3A
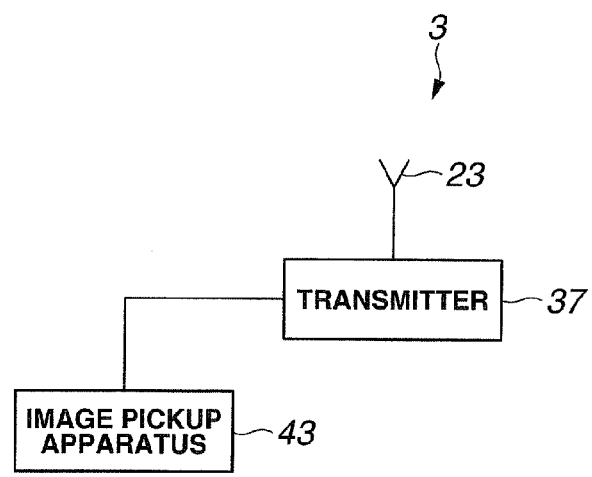

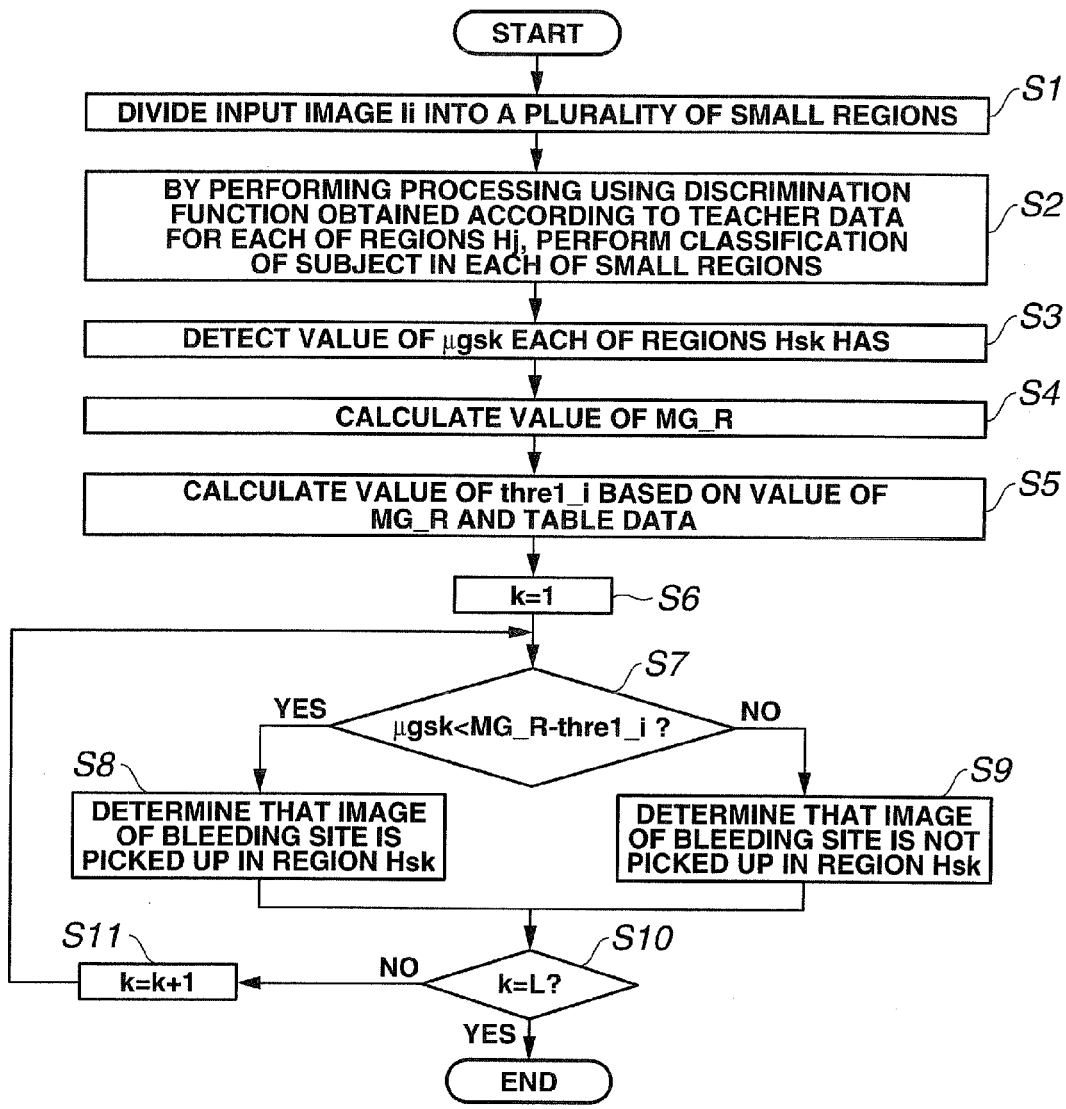
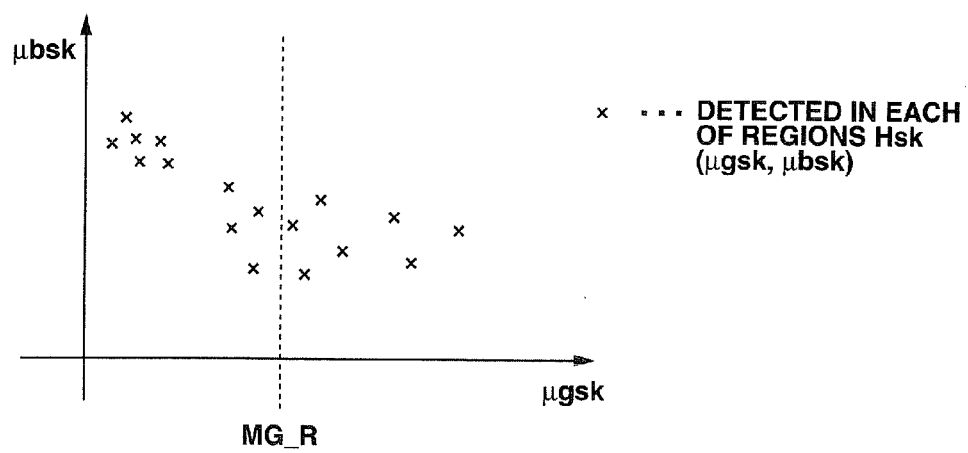

▧ ··· ORIGINAL REGION DETECTED AS BLEEDING SITE

▦ ··· EXTENDED REGION

MEDICAL IMAGE PROCESSING DEVICE AND MEDICAL IMAGE PROCESSING METHOD

CROSS REFERENCE TO RELATED APPLICATION

This application is a continuation application of PCT/JP2007/063483 filed on Jul. 5, 2007 and claims benefit of Japanese Application No. 2006-216250 filed in Japan on Aug. 8, 2006, the contents of which are incorporated herein by this reference.

BACKGROUND OF INVENTION

1. Field of the Invention

The present invention relates to a medical image processing device and a medical image processing method, and particularly, to a medical image processing device and a medical image processing method which are capable of detecting a lesion site showing a red color.

2. Description of the Related Art

Conventionally, in a medical field, observation with use of image pickup apparatuses such as an X-ray diagnostic apparatus, CT, MRI, an ultrasound observation apparatus and an endoscope apparatus has been widely performed. Of such image pickup apparatuses, an endoscope apparatus has, for example, an elongated insertion section which is inserted into a body cavity, and has the operation and configuration of picking up the image of the inside of a body cavity which is formed by an objective optical system disposed at the distal end portion of the insertion section by an image pickup unit such as a solid state image pickup element, outputting the image as an image pickup signal, and displaying the image of the inside of the body cavity on a display unit such as a monitor based on the image pickup signal. A user observes an organ and the like in the body cavity, for example, based on the image of the inside of the body cavity displayed on the display unit such as a monitor.

Further, the endoscope apparatus can directly pick up the image of the mucosa of a digestive tract. Therefore, the user can comprehensively observe various findings such as, for example, the color tone of a mucosa, shape of a lesion, and microscopic structures of the surface of a mucosa.

In recent years, as the image pickup apparatus which can be expected to have usefulness substantially the same as that of the aforementioned endoscope apparatus, for example, capsule type endoscope apparatuses have been proposed. A capsule type endoscope apparatus is generally configured by a capsule type endoscope which is disposed in a body cavity by being swallowed by a subject from his or her mouth, and transmits the image of the inside of the body cavity which is picked up to an outside as an image pickup signal, a receiver which receives the transmitted image pickup signal outside the body cavity, and thereafter, accumulates the received image pickup signal, and an observation device for observing the image of the inside of the body cavity based on the image pickup signal accumulated in the receiver.

Further, an endoscope apparatus also can detect a predetermined image including a bleeding site, by using the image processing method described in, for example, International Publication No. WO02/073507, as the image processing method capable of detecting a predetermined image including a lesion site such as a bleeding site.

The method for detecting calorimetric abnormalities within a living body which is the image processing method described in International Publication No. WO02/073507, is the method for making it possible to detect a predetermined image including a bleeding site by detecting a bleeding site for each divided region of the image based on the distance from each average value in the feature space in which the color tone is set as a feature value, by paying attention to the difference in color tone between a normal mucosa and a bleeding site.

SUMMARY OF THE INVENTION

A medical image processing device of the present invention has an image dividing unit which divides an image corresponding to a subject image which is picked up by a medical image pickup apparatus into a plurality of regions constituted of at least one or more pixels, a feature value calculating unit which calculates a color tone feature value which is a feature value based on a color tone of the image in each of the plurality of regions, a first color tone reference value calculating unit which calculates a first color tone reference value based on the color tone feature value which each of the plurality of regions has, a first lesion detection reference calculating unit which properly calculates a first lesion detection reference for detecting a lesion finding in accordance with the first color tone reference value, and a first image region detecting unit which detects a first target region that is a region in which an image of the lesion finding is picked up among the respective plurality of regions, based on the first lesion detection reference and the color tone feature value which each of the plurality of regions has.

A medical image processing method of the present invention has an image dividing step of dividing an image corresponding to a subject image which is picked up by a medical image pickup apparatus into a plurality of regions constituted of at least one or more pixels, a feature value calculating step of calculating a color tone feature value which is a feature value based on a color tone of the image in each of the plurality of regions, a first color tone reference value calculating step of calculating a first color tone reference value based on the color tone feature value which each of the plurality of regions has, a first lesion detection reference calculating step of properly calculating a first lesion detection reference for detecting a lesion finding in accordance with the first color tone reference value, and a first image region detecting step of detecting a first target region that is a region in which an image of the lesion finding is picked up among the respective plurality of regions, based on the first lesion detection reference and the color tone feature value which each of the plurality of regions has.

BRIEF DESCRIPTION OF THE DRAWINGS

FIG. 1 is an external front view showing appearance of a medical image processing device in which an image processing operation which is the first embodiment of the present invention is performed, and peripheral devices;

FIG. 2 is an essential part enlarged sectional view showing a part of a capsule type endoscope which generates predetermined image information to be processed in the medical image processing device of the first embodiment by cutting out the part;

FIG. 3A is a diagram showing an outline of a configuration of an electric system relating to transmission and reception of a signal in the capsule type endoscope of a capsule type endoscope apparatus, which supplies the predetermined image information to the medical image processing device of the first embodiment;

FIG. 11 is a flowchart showing one example of a procedure of processing carried out in the first embodiment by the medical image processing device of FIG. 1;

FIG. 12 is a schematic diagram of each data obtained when the processing of the flowchart of FIG. 11 is performed;

DETAILED DESCRIPTION OF THE PREFERRED EMBODIMENT(S)

Hereinafter, embodiments of the present invention will be described with reference to the drawings.
(First Embodiment)

Figure 3B:
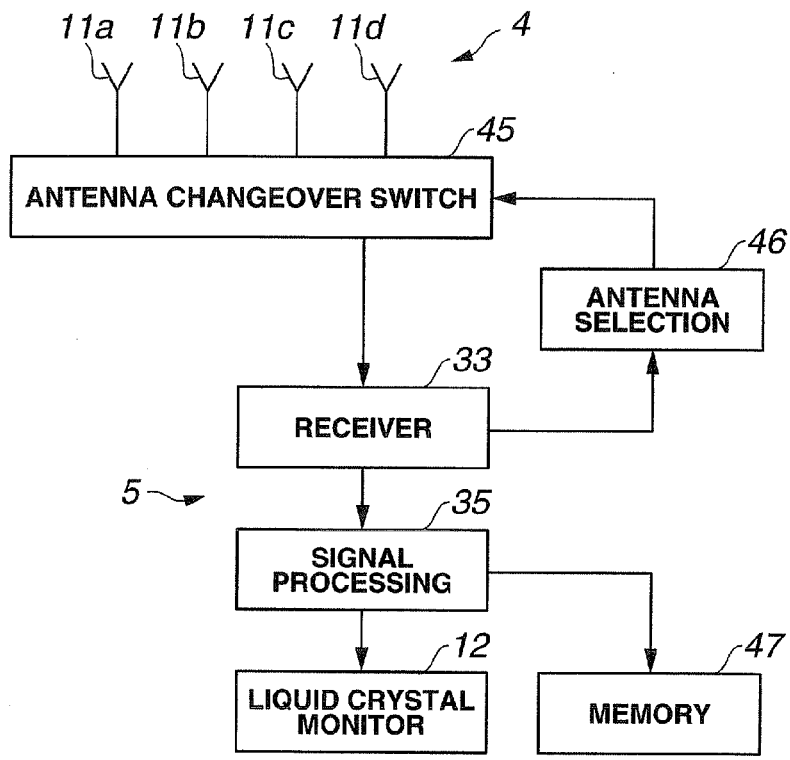
FIG. 3B is a diagram showing an outline of a configuration of an electric system relating to transmission and reception of a signal in an extracorporeal device of the capsule type endoscope apparatus which supplies the predetermined image information to the medical image processing device of the first embodiment.
Figure 4:
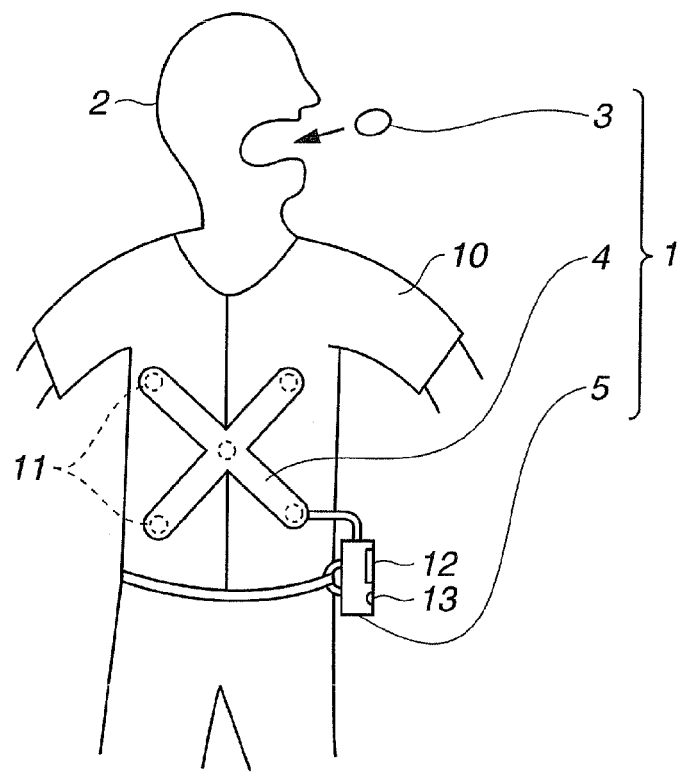
FIG. 4 is a view showing one use example of the capsule type endoscope apparatus which supplies predetermined image information to the medical image processing device of the first embodiment.
Figure 5:
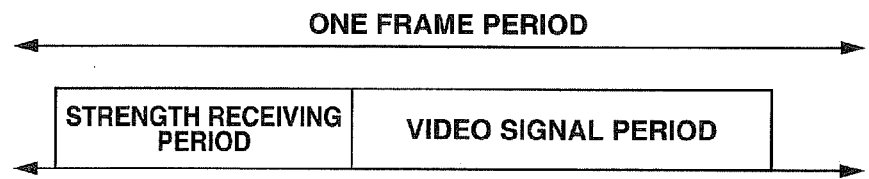
FIG. 5 is a timing chart showing one example of a signal which is outputted from the capsule type endoscope shown in FIG. 2.
Figure 6:
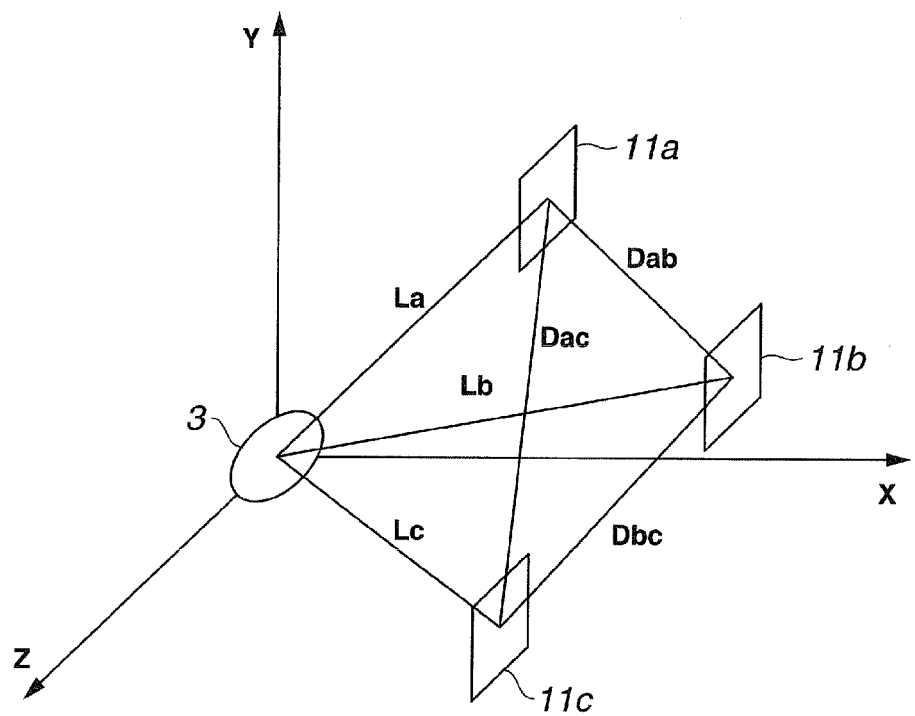
FIG. 6 is an explanatory diagram explaining position detection of the capsule type endoscope shown in FIG. 2.
Figure 7:
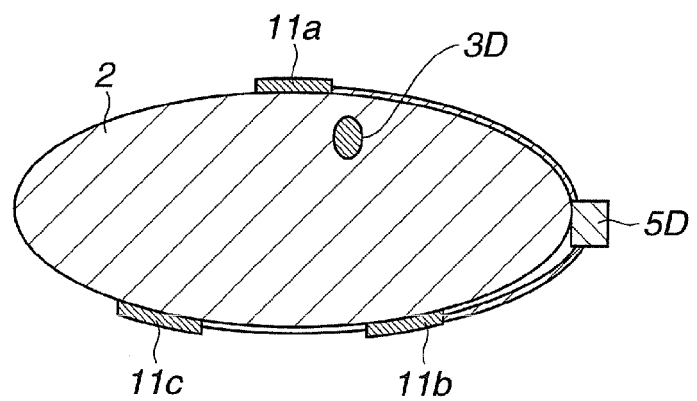
FIG. 7 is an essential part enlarged sectional view showing an antenna unit at a time of using the capsule type endoscope apparatus shown in FIG. 4.
Figure 8:
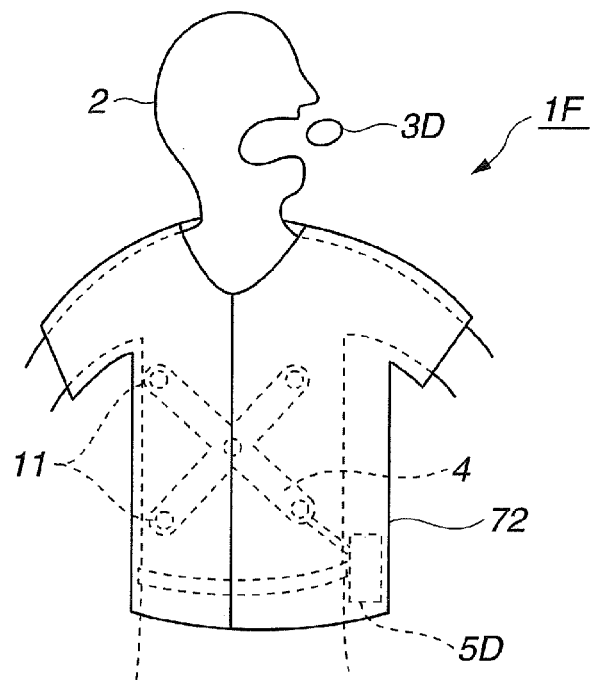
FIG. 8 is an explanatory view explaining a shield jacket at the time of using the capsule type endoscope apparatus shown in FIG. 4.
Figure 9:
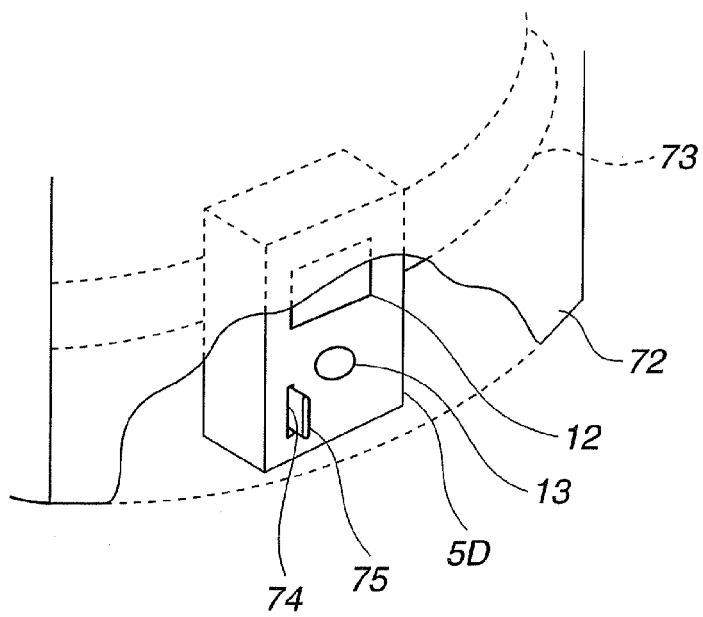
FIG. 9 is an explanatory view explaining a fitting state of an external device of the capsule type endoscope apparatus shown in FIG. 4 to a subject.
Figure 10:
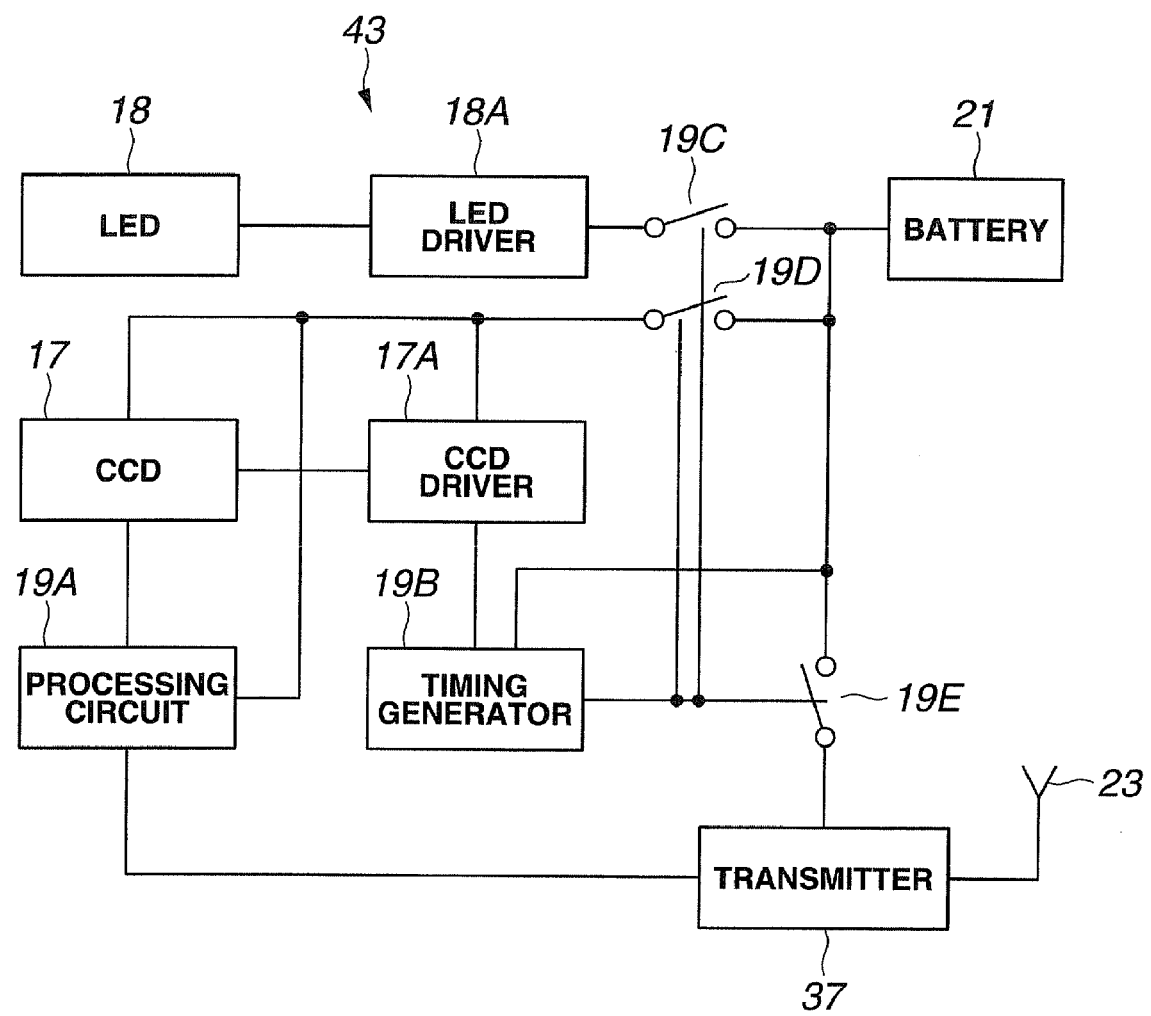
FIG. 10 is a block diagram showing an electric configuration of the capsule type endoscope shown in FIG. 2.

Hereinafter, a first embodiment of the present invention will be described with reference to the drawings. FIG. 1 is an external front view showing appearance of a medical image processing device in which an image processing operation which is the first embodiment of the present invention is performed, and peripheral devices. FIG. 2 is an essential part enlarged sectional view showing a part of a capsule type endoscope which generates predetermined image information to be processed in the medical image processing device of the first embodiment by cutting out the part. FIG. 3A is a diagram showing an outline of a configuration of an electric system relating to transmission and reception of a signal in the capsule type endoscope of a capsule type endoscope apparatus, which supplies the predetermined image information to the medical image processing device of the first embodiment. FIG. 3B is a diagram showing an outline of a configuration of an electric system relating to transmission and reception of a signal in an extracorporeal device of the capsule type endoscope apparatus which supplies the predetermined image information to the medical image processing device of the first embodiment. FIG. 4 is a view showing one use example of the capsule type endoscope apparatus which supplies predetermined image information to the medical image processing device of the first embodiment. FIG. 5 is a timing chart showing one example of a signal outputted from the capsule type endoscope shown in FIG. 2. FIG. 6 is an explanatory diagram explaining position detection of the capsule type endoscope shown in FIG. 2. FIG. 7 is an essential part enlarged sectional view showing an antenna unit at a time of using the capsule type endoscope apparatus shown in FIG. 4. FIG. 8 is an explanatory view explaining a shield jacket at the time of using the capsule type endoscope apparatus shown in FIG. 4. FIG. 9 is an explanatory view explaining a fitting state of an external device of the capsule type endoscope apparatus shown in FIG. 4 to a subject. FIG. 10 is a block diagram showing an electric configuration of the capsule type endoscope shown in FIG. 2.

Figure 13:
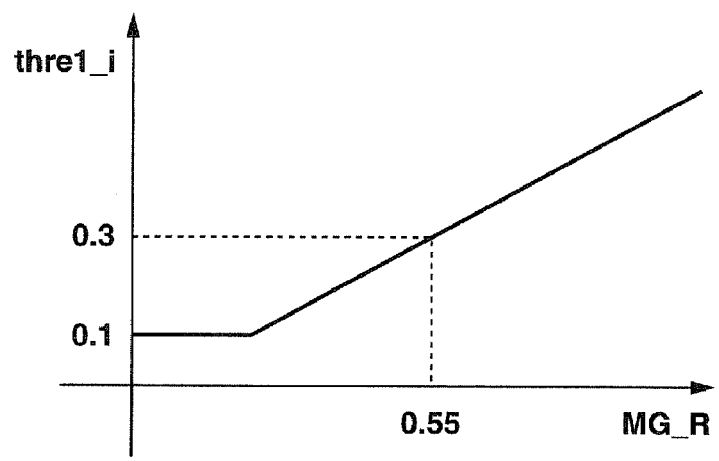
FIG. 13 is a diagram showing one example of relationship between MG_R and thre1_i which are values used in the processing in the flowchart of FIG. 11.
Figure 14:
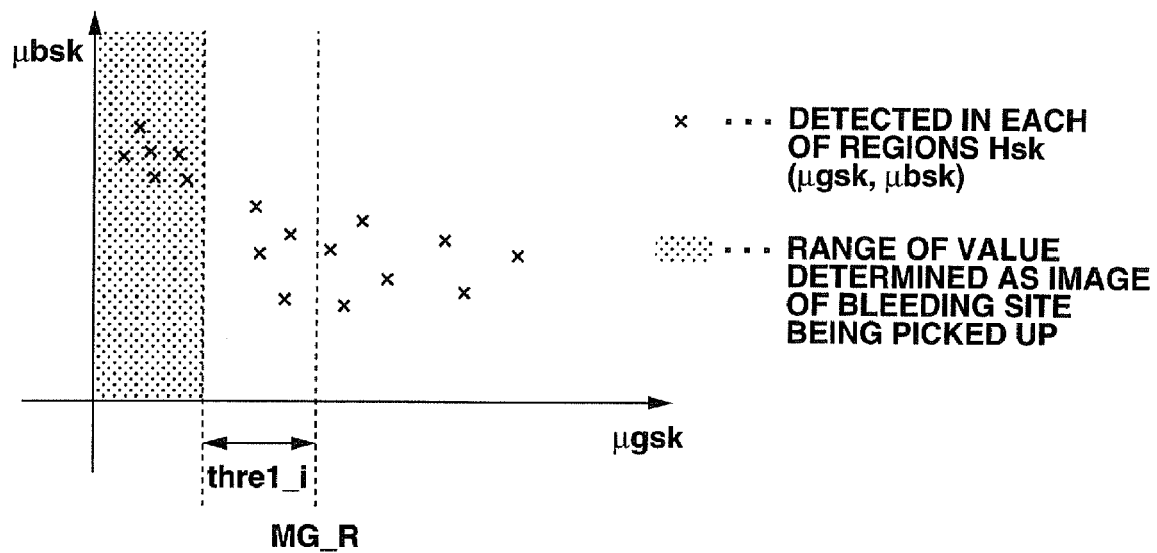
FIG. 14 is a diagram showing a range of a value which is determined as an image of a bleeding site being picked up when the processing of the flowchart of FIG. 11 is performed.

Further, FIG. 11 is a flowchart showing one example of a procedure of processing carried out in the first embodiment by the medical image processing device of FIG. 1. FIG. 12 is a schematic diagram of each data obtained when the processing of the flowchart of FIG. 11 is performed. FIG. 13 is a diagram showing one example of relationship between MG_R and thre1_i which are values used in the processing of the flowchart of FIG. 11. FIG. 14 is a diagram showing a range of a value which is determined as an image of a bleeding site being picked up when the processing of the flowchart of FIG. 11 is performed.

In a capsule type endoscope apparatus 1 which supplies predetermined image information to the image processing device which is the first embodiment of the present invention, a main part is configured by having a capsule type endoscope 3, an antenna unit 4 and an external device 5 as shown in FIG. 4.

The capsule type endoscope 3 as a medical image pickup apparatus is formed into a shape for traveling in a digestive tract by peristaltic movement after disposed in a body cavity by being swallowed into the body cavity from a mouth of a patient 2 that is a subject, though the details will be described later. The capsule type endoscope 3 has therein an image pickup function of picking up an image of the inside of the body cavity and generating the image information of the picked-up image, and a transmission function of transmitting the image information of the picked-up image outside the body. The antenna unit 4 is placed on a body surface of the patient 2, and has a plurality of receiving antennas 11 which receive the image information of the picked-up image transmitted from the aforementioned capsule type endoscope 3, though the details will be described later. The external device 5 has an outer shape formed into a box shape, and has the functions of various kinds of processing of the image information of the picked-up image received by the aforementioned antenna unit 4, recording of the image information of the picked-up image, display of the image of the picked-up image based on the image information of the picked-up image, and the like, though the details will be described later. A liquid crystal monitor 12 for displaying the aforementioned image of the picked-up image, and an operation section 13 for making an operation instruction of various functions are provided on a surface of a package of the external device 5.

Further, in the external device 5, an LED for displaying warning concerning a residue of a battery for a drive power supply, and the operation section 13 constituted of a switch such as a power supply switch are provided on the surface of the package. Further, an arithmetic operation executing section using a CPU and a memory is provided inside the capsule type endoscope 3, and the capsule type endoscope 3 may be configured so that, for example, in the arithmetic operation executing section, image processing that will be described later is executed for the image information of the picked-up image which is received and recorded.

The external device 5 is attachably and detachably fitted to the body of the patient 2. The external device 5 is fitted in a cradle 6 as shown in FIG. 1, and thereby, connected to the medical image processing device (hereinafter, described as a terminal device) 7 which is the first embodiment of the present invention to be attachable and detachable. For the terminal device 7, for example, a personal computer is used, and the terminal device 7 has a terminal main body 9 having a processing function and a storage function of various data, a keyboard 8a and a mouse 8b for inputting various kinds of operation processing, and a display 8c for displaying various processing results. As a basic function, the terminal device 7 has the function of performing image processing of, for example, taking in image information of a picked-up image recorded in the aforementioned external device 5 via the cradle 6, writing and recording the information into a rewritable memory contained in the terminal main body 9 or a portable memory such as a rewritable semiconductor memory attachable to and detachable from the terminal main body 9, and displaying the recorded image information of the picked-up image on the display 8c. The image information of the picked-up image stored in the aforementioned external device 5 may be taken into the terminal device 7 by a USB cable or the like instead of the aforementioned cradle 6.

The image processing which the terminal device 7 performs is performed in a control section 9a, which the terminal main body 9 has, as, for example, processing of selecting an image to be displayed in accordance with an elapsed time from the image information of the picked-up image taken in from the aforementioned external device 5 and recorded, and image processing which will be described later. The control section 9a has a CPU (central processing unit) or the like, and can temporarily retain the processing result in a register or the like not illustrated, for example, when the processing as mentioned above is performed.

Next, an outer shape and an internal structure of the above described capsule type endoscope 3 will be described by using FIG. 2. The capsule type endoscope 3 has a package member 14 which is U-shaped in section, and a substantially semi spherical cover member 14a which is fitted to an open end of a distal end side of the package member 14 by an adhesive to be watertight, and formed from a transparent member. Therefore, the package of the capsule type endoscope 3 is formed to have a watertight structure and a capsule shape in a state in which the package member 14 and the cover member 14a are connected.

In a portion which is a hollow portion inside the capsule shape having the package member 14 and the cover member 14a, and is a portion corresponding to a substantial center of a semispherical arc of the aforementioned cover member 14a, an objective lens 15 which takes in an observation site image which is incident via the cover member 14a is disposed by being stored in a lens frame 16. A charge coupled device (hereinafter, described as a CCD) 17 that is an image pickup device is disposed in an image forming position of the objective lens 15. Further, four LEDs 18 of a white color system which emit and irradiate illumination light are disposed on the same plane around the lens frame 16 storing the aforementioned objective lens 15 (only two LEDs are illustrated in the drawing). In the hollow portion inside the aforementioned package member 14 at a rear end side of the aforementioned CCD 17, a processing circuit 19 which performs processing of generating an image pickup signal which is photoelectric-converted by performing drive control of the aforementioned CCD 17, and generating an image signal of the picked-up image by applying predetermined signal processing to the image pickup signal, and processing of LED drive for controlling operation of lighting/non-lighting of the aforementioned LED 18, a communication processing circuit 20 which converts the image signal of the picked-up image generated by the image pickup processing of the processing circuit 19 into a radio signal and transmits the radio signal, a transmitting antenna 23 which transmits the radio signal from the communication processing circuit 20 to an outside, and a plurality of button batteries 21 which supply a driving power supply for the aforementioned processing circuit 19 and communication processing circuit 20.

The CCD 17, the LED 18, the processing circuit 19, the communication processing circuit 20 and the transmitting antenna 23 are disposed on substrates not illustrated, and the substrates are connected by a flexible substrate not illustrated. Further, the aforementioned processing circuit 19 is equipped with an arithmetic circuit not illustrated for performing image processing that will be described later. More specifically, the aforementioned capsule type endoscope 3 has an image pickup apparatus 43 having the aforementioned CCD 17, LED 18 and processing circuit 19, a transmitter 37 having the aforementioned communication processing circuit 20, and the transmitting antenna 23, as shown in FIG. 3A.

Next, the detailed configuration of the image pickup apparatus 43 of the aforementioned capsule type endoscope 3 will be described by using FIG. 10. The image pickup apparatus 43 is constituted of an LED driver 18A which controls the operation of lighting/non-lighting of the LED 18, a CCD driver 17A for controlling drive of the CCD 17 to transfer electric charges which are photoelectric-converted, a processing circuit 19A which generates an image pickup signal by using the electric charges transferred from the aforementioned CCD 17 and generates an image signal of the picked-up image by applying predetermined signal processing to the image pickup signal, a switch section which supplies a drive power supply from the battery 21 to the aforementioned LED driver 18A, CCD driver 17A, processing circuit 19A and transmitter 37, and a timing generator 19B which supplies a timing signal to the aforementioned switch section and the CCD driver 17A. The aforementioned switch section is constituted of a switch 19C which turns on/off power supply to the aforementioned LED driver 18A from the battery 21, a switch 19D which turns on/off power supply to the aforementioned CCD 17, CCD driver 17A and processing circuit 19A, and a switch 19E which turns on/off power supply to the aforementioned transmitter 37. Further, drive power is always supplied to the aforementioned timing generator 19B from the battery 21.

In the image pickup apparatus 43 of the capsule type endoscope 3 having such a configuration, when the switch 19C, the switch 19D and the switch 19E are in the off state, each section except for the timing generator 19B is in an non-operating state. When a timing signal is outputted from the timing generator 19B, the aforementioned switch 19D is turned on, and thereby, the CCD 17, the CCD driver 17A and the processing circuit 19A which are supplied with power from the battery 21 are brought into an operating state.

After an electronic shutter of the CCD 17 is operated, and an unnecessary dark current is removed at the time of the beginning of drive of the aforementioned CCD 17, the timing generator 19B turns on the switch 19C to drive the LED driver 18A to light the LED 18 to expose the CCD 17. The LED 18 is lit for a predetermined time required for exposure of the CCD 17, and thereafter, the LED 18 is extinguished at the timing when the switch 19C is turned off for reduction of the power consumption.

The electric charges which are stored within the aforementioned predetermined time in which exposure of the aforementioned CCD 17 is performed are transferred to the processing circuit 19A by control of the CCD driver 17A. The processing circuit 19A generates an image pickup signal based on the electric charge transferred from the CCD 17, and applies predetermined signal processing to the image pickup signal to generate an endoscope image signal. For example, when the signal transmitted from the transmitter 37 is of an analog radio type, the processing circuit 19A generates an analog image pickup signal in which a composite synchronizing signal is superimposed on a CDS output signal, and thereafter, outputs the analog image pickup signal to the transmitter 37 as the endoscope image signal. Further, for example, when the signal transmitted from the transmitter 37 is of a digital radio type, the processing circuit 19A generates a digital image signal of a picked-up image in which coding processing such as scramble is applied to a serial digital signal generated by an analog/digital converter, and outputs the digital image signal of the picked-up signal to the transmitter 37 as the endoscope image signal.

The transmitter 37 applies modulation processing to the analog image signal of a picked-up image or the digital image signal of a picked-up image, which is the endoscope image signal supplied from the aforementioned processing circuit 19A, and transmits the signal by radio to the outside from the transmitting antenna 23. At this time, the switch 19E is turned on/off by the timing generator 19B so that the drive electric power is supplied to the transmitter 37 only at the timing in which the image signal of a picked-up image is outputted from the aforementioned processing circuit 19A.

The switch 19E may be controlled so that the drive electric power is supplied to the transmitter 37, after a predetermined time elapses after the image signal of a picked-up image is outputted from the processing circuit 19A. Further, the switch 19E may have the configuration so as to be controlled to supply electric power to the transmitter 37, when inserted into the body cavity of the patient 2 that is a subject, in accordance with a signal which is outputted from the timing generator 19B based on the detection results of detection of a predetermined pH value by a pH sensor not illustrated, detection of humidity of a predetermined value or more by a humidity sensor not illustrated, detection of pressure or acceleration of a predetermined value or more by a pressure sensor not illustrated or an acceleration sensor not illustrated, and the like, the sensors being provided in the capsule type endoscope 3.

The image pickup apparatus 43 of the aforementioned capsule type endoscope 2 generally picks up two images per second (two frames per second=2 fps), but, for example, in the case of inspection of an esophagus, the image pickup apparatus 43 can pick up 15 to 30 images per second (15 fps to 30 fps). More specifically, by providing the capsule type endoscope 3 with a timer circuit not illustrated, and by the timer circuit, drive of the image pickup apparatus 43 is controlled so as to perform high-speed image pickup with the number of images picked up per second being large within a predetermined time of the timer count, and perform low-speed image pickup with the number of images picked up per second being small after a predetermined time lapses, for example. Alternatively, with input of the power supply of the capsule type endoscope 3, the timer circuit is operated, and by the timer circuit, drive of the image pickup apparatus 43 can be controlled so as to perform high-speed image pickup until the time after the endoscope passes through the esophagus directly after the patient 2 swallows the endoscope, for example. Further, the capsule type endoscope for low-speed image pickup, and the capsule type endoscope for high-speed image pickup may be separately provided, and may be used in accordance with the observation target site.

Next, the antenna unit 4 which is placed on the body surface of the aforementioned patient 2 will be described. As shown in FIG. 4, when the patient 2 swallows the capsule type endoscope 3, and undergoes endoscopy, the patient 2 puts on a jacket 10 in which the antenna unit 4 constituted of a plurality of receiving antennas 11 is installed. In the antenna unit 4, as shown in FIG. 7, a plurality of receiving antennas 11 each having unilateral directivity such as a patch antenna used for GPS, for example, are disposed with their directivity oriented in the direction of the inside of the body of the patient 2. More specifically, the capsule main body 3D of the capsule type endoscope 3 is held in the body, and therefore, the aforementioned plurality of antennas 11 are disposed to surround the capsule main body 3D inside the body. By using the antenna 11 with high directivity, the antenna unit is insusceptible to be influenced by interference and jamming by radio waves from the matters other than the capsule main body 3D inside the body.

The aforementioned jacket 10 is constituted of the aforementioned antenna unit 4 installed on the body surface of the patient 2, and a shield jacket 72 formed of electromagnetic shielding fibers so as to cover the main body section 5D of the external device 5 placed on the waist of the patient 2 with a belt, as shown in FIG. 8. For the electromagnetic shielding fibers forming the shield jacket 72, metal fibers, metal chemical fibers, copper sulfide-containing fibers and the like are used. The shape of the shield jacket 72 is not limited to the jacket shape, but it may be the shape of a vest, a one-piece dress or the like, for example.

As an example of fitting the aforementioned external device 5 to the aforementioned shield jacket 72, as shown in FIG. 9, a keyhole 74 is provided in the external main body 5D of the aforementioned external device 5, and by a key 75 which is provided in the aforementioned shield jacket 72 being inserted into the aforementioned keyhole 74, the shield jacket 72 can be attachably and detachably fitted to the belt 73. Alternatively, a pocket not illustrated is simply provided in the shield jacket 72, and the external main body 5D may be stored in the pocket, or a magic tape (registered trademark) is placed on the external main body 5D of the external device 5 and the shield jacket 72, and the shield jacket 72 and the external main body 5D are attached and fixed by the magic tape (registered trademark).

More specifically, by fitting the shield jacket 72 to the body on which the antenna unit 4 is disposed, the radio waves from the outside to the antenna unit 4 is shielded and blocked, and the antenna unit 4 is further insusceptible to be influenced by interference and jamming by the external radio waves.

Next, the configurations of the aforementioned antenna unit 4 and the external device 5 will be described by using FIG. 3B. The aforementioned antenna unit 4 is constituted of a plurality of receiving antennas 11a to 11d which receive a radio signal transmitted from the transmitting antenna 23 of the aforementioned capsule type endoscope 3, and an antenna changeover switch 45 which switches the antennas 11a to 11d. The aforementioned external device 5 is constituted of a receiving circuit 33 which performs reception processing such as conversion of a radio signal from the changeover switch 45 into an image signal of a picked-up image, and amplification, a signal processing circuit 35 which applies predetermined signal processing to the image signal of a picked-up image supplied from the receiving circuit 33, and generates a signal for displaying the image of the picked-up image, and image data of the picked-up image, a liquid crystal monitor 12 which displays the image of the picked-up image based on the signal for displaying an image of a picked-up image, which is generated by the signal processing circuit 35, a memory 47 which stores the image data of the picked-up image generated by the aforementioned signal processing circuit 35, and an antenna selecting circuit 46 which controls the aforementioned antenna changeover switch 45 in accordance with the magnitude of the radio signal which is subjected to reception processing by the aforementioned receiving circuit 33.

The plurality of receiving antennas 11 of the aforementioned antenna unit 4, which are illustrated as the receiving antennas 11a to 11d in the drawing, receive the radio signal transmitted with fixed radio field intensity from the transmitting antenna 23 of the aforementioned capsule type endoscope 3. As for the plurality of receiving antennas 11a to 11d, the antenna changeover switch 45 is controlled in accordance with the antenna selecting signal from the antenna selecting circuit 46 of the aforementioned external device 5, and the receiving antenna which receives the aforementioned radio signal is sequentially switched. More specifically, the radio signal which is received by each of the receiving antennas 11a to 11d which are sequentially switched by the aforementioned antenna changeover switch 45 is outputted to the aforementioned receiver 33. In the receiver 33, the reception strength of the radio signal of each of the receiving antennas 11a to 11d is detected, the positional relationship of each of the receiving antennas 11a to 11d and the capsule type endoscope 3 is calculated, demodulation processing is performed for the radio signal, and the image signal of the picked-up image is outputted to the signal processing circuit 35. The aforementioned antenna selecting circuit 46 is controlled by the output from the aforementioned receiver 33.

An operation of the antenna changeover switch 45 by the aforementioned antenna selecting circuit 46 will be described. The radio signal transmitted from the aforementioned capsule type endoscope 3 is assumed to be transmitted with a strength receiving period which is a transmission period of a reception strength signal indicating reception strength of the radio signal, and a video signal period which is a transmission period of an image signal of a picked-up image being sequentially repeated in a transmission period of one frame for an image signal of a picked-up image as shown in FIG. 5.

The aforementioned antenna selecting circuit 46 is supplied with reception strength of a reception strength signal received by each of the receiving antennas 11a to 11d via the aforementioned receiving circuit 33. The aforementioned antenna selecting circuit 46 compares the strength of the reception strength signals of the respective antennas 11a to 11d supplied from the aforementioned receiver 33, determines the optimal receiving antenna for receiving the image signal of a picked-up image in the video signal period, namely, an antenna 11i (i=a to d) with the highest strength of the reception strength signal, and generates and outputs a control signal for causing the antenna changeover circuit 45 to switch the antenna to the antenna 11i. Thereby, when the reception strength of the reception strength signal of the other antenna is higher than the antenna which presently receives the image signal, the receiving antenna in the video signal period is switched from the next frame.

Thus, each time the radio signal from the capsule type endoscope 3 is received, the reception strength of the image signal of a picked-up image or the reception strength signals is compared, and the antenna 11i with the highest reception strength is designated as the antenna for receiving an image signal by the antenna selecting circuit 46 which receives the comparison result. Thereby, even if the capsule type endoscope 3 moves inside the body of the patient 2, an image signal can be received which is obtained by the antenna 11 which can detect the signal with the highest reception strength in its moved position. Further, the inside of a body is divided into a portion where the moving speed of the capsule type endoscope 3 is very low, and a portion where it is very high. Therefore, antenna switching operation is not always performed once for each image pickup operation, and the antenna switching operation may be performed once for a plurality of image pickup operations in the high-speed image pickup mode or the like.

The capsule type endoscope 3 moves inside the body of the patient 2. Therefore, a detection result signal which is the result of detecting the radio wave strength is transmitted from the external device 5 at proper time intervals, and based on the signal, the output at the time of transmission of the capsule type endoscope 3 may be updated. In this way, even when the capsule type endoscope 3 moves inside the body of the patient 2, proper transmission output can be set, consumption of useless energy of the battery 21 or the like can be prevented, and the transmission and reception state of signals can be kept in a proper state.

Next, a method for acquiring information indicating positional relationship of the aforementioned plurality of receiving antennas 11 and the capsule type endoscope 3 will be described by using FIG. 6. In FIG. 6, the case in which the capsule type endoscope 3 is set at the origin of a three-dimensional coordinates X, Y and Z will be described as an example. For simplification of the description, the three receiving antennas 11a, 11b and 11c are used among the aforementioned plurality of receiving antennas 11a to 11d. A distance between the receiving antenna 11a and the receiving antenna 11b is set as Dab, a distance between the receiving antenna 11b and the receiving antenna 11c is set as Dbc, and a distance between the receiving antenna 11a and the receiving antenna 11c is set as Dac. Further, the receiving antennas 11a to 11c and the capsule type endoscope 3 are in predetermined distance relation.

As for the radio signal with fixed transmission strength of the capsule type endoscope 3, which is transmitted, the reception strength when the radio signal is received by each of the receiving antennas $11j$ (j=a, b and c) is the function of a distance Li (i=a, b and c) from the capsule type endoscope 3 (the transmitting antenna 23 of the capsule type endoscope 3). More specifically, the reception strength depends on the distance Li accompanied by a radio attenuation amount. Accordingly, from the reception strength received by the receiving antenna $11j$ of the radio signal transmitted from the capsule type endoscope 3, the distance Li between the capsule type endoscope 3 and each receiving antenna $11j$ is calculated. For calculation of the distance Li, relation data of the attenuation amount of the radio wave in accordance with the distance between the aforementioned capsule type endoscope 3 and the receiving antenna $11j$ and the like are set in the aforementioned antenna selecting circuit 46 in advance. The calculated distance data indicating the positional relationship of the capsule type endoscope 3 and each receiving antenna $11j$ is stored in the aforementioned memory 47 as the positional information of the capsule type endoscope 3. In an image information processing method which will be described later by the aforementioned terminal device 7 based on the image information of an picked-up image and the positional information of the capsule type endoscope 3 which are stored in the memory 47, the information is useful for setting the position of the findings by endoscope observation.

Next, an image processing operation of the present embodiment will be described.

In the present embodiment, an image of an inside of a body cavity which is picked up by the capsule type endoscope 3 is assumed to have the value which satisfies the number of pixels N in an X-axis direction×the number of pixels N in a y-axis direction ($1 \leq N$) and to be constituted of three planes of R (red), G (green) and B (blue). Further, each of the pixels in each of the planes of R (red), G (green) and B (blue) takes 8 bits, namely, a value from zero to 255 as the RGB value which is a gray level value. Further, in the embodiment of the present invention, the $i^{th}$ image in A of images ($1 \leq A$) which are successively picked up in a time series is expressed as Ii ($1 \leq i \leq A$). Further, in the present embodiment, the $v^{th}$ pixels ($1 \leq v \leq N \times N$) in the respective planes of the image Ii are expressed as riv, giv and biv, respectively.

The image processing operation of the present embodiment is performed as the processing in a control section 9a which the terminal main body 9 of the aforementioned terminal device 7 has.

First, the control section 9a as an image dividing unit divides the image Ii having the size of N×N (number of pixels) into a plurality of rectangular regions each having a predetermined size, namely, ($N^2/M^2$) (a plurality) of small regions each having the size of M×M (M<N) (step S1 of FIG. 11). In the following description, out of the small regions divided in the control section 9a, one small region is expressed as Hj ($1 \leq j \leq N^2/M^2$). Further, the size of the image which is inputted into the control section 9a, and the size of the small region when the image is divided are not limited to the aforementioned sizes as long as they are the sizes to which the processing which will be described hereinafter is applicable, and for example, the size may be a pixel unit (M=1).

Next, the control section 9a as an image region classifying unit performs classification of a subject in each of the regions Hj by performing processing with use of discriminating means such as a discriminant function based on the Bayesian discrimination rule, for example, which is obtained in accordance with teacher data for each of the regions Hj (step S2 of FIG. 11). Thereby, the control section 9a classifies the respective regions Hj into, for example, a non-biological mucosa class as a region group in which the images of subjects such as feces and bubbles are picked up, and a biological mucosa class as a region group in which the images of subjects such as a gastric mucosa and villi are picked up, and performs the following processing while holding the classification result.

Here, a concrete example of the processing shown in step S2 of FIG. 11 will be described in detail hereinafter.

The control section 9a calculates color tone information reflecting the difference in color on the image of the image of an object to be picked up, and texture information reflecting the difference in structure on the image of the image of an object to be picked up as a color tone feature value and a texture feature value, in each of the divided regions Hj.

In the present embodiment, the color tone feature value which is calculated by the control section 9a is the value expressed as two feature values constituted of the average value of giv/riv (hereinafter, described as μgj) and the average value of biv/giv (hereinafter, described as μbj) as the values based on the ratio of the RGB values of each pixel included in the region Hj. Each of the values of μgj and μbj takes a value from 0 to 1. Further, each of the values of μgj and μbj takes a small value substantially similarly in the region showing a relatively red color tone such as a gastric mucosa, for example. Meanwhile, each of the values of μgj and μbj takes a large value substantially similarly in the region showing a relatively white color tone such as a small intestine, for example. Further, each of the values of μgj and μbj takes a value which satisfies μgj>μbj in a region showing a relatively yellow color tone such as feces, for example.

In the present embodiment, the texture feature value which is calculated by the control section 9a reflects the difference in structure on the image of the image of an object to be picked up. The structure on the image of the image of the object to be picked up is shown as, for example, a microscopic structure of villi in the mucosal surface and the like, a protean pattern which feces have and the like. More specifically, the texture feature values calculated by the control section 9a are variation coefficients CVrj, CVgj and CVbj of the RGB values shown as the three feature values, which are obtained by dividing standard deviations σrj, σgj and σbj of the RGB values of each of the pixels included in the region Hj by average values mrj, mgj and mbj of the RGB values of each of the pixels included in the region Hj. The calculation formulas for calculating the variation coefficients CVrj, CVgj and CVbj are expressed as the following formulas (1), (2) and (3).

$$CVrj = \sigma rj/mrj \quad (1)$$

$$CVgj = \sigma gi/mgj \quad (2)$$

$$CVbj = \sigma bj/mbj \quad (3)$$

By the variation coefficients CVrj, CVgj and CVbj which are calculated from the above described formula (1), formula (2) and formula (3), the degree of the pixel variation according to the texture structure can be digitized without being influenced by the difference in illumination light amount or the like supplied to an image pickup object. Each of the values of CVrj, CVgj and CVbj takes a small value substantially similarly since a clear texture structure is not present in a region in which the structure on the image is relatively flat such as a gastric mucosa of which image is picked up in normal observation, for example, in a state where magnified observation is not performed. Meanwhile, each of the values of CVrj, CVgj and CVbj takes a large value substantially similarly in a region in which relatively many edges are included in the structure on the image, such as villi of a small intestine, for example.

The control section 9a as a feature value calculating unit calculates five feature values constituted of a color tone feature value and a texture feature value, namely, each of the values of µgj, µbj, CVrj, CVgj and CVbj, in each of $N^2/M^2$ of regions Hj, based on the RGB values of each of the pixels except for halation pixels and dark pixels. In the present embodiment, when the ratio of the sum of the number of halation pixels and the number of dark pixels exceeds 50%, for example, in M×M pixels which the regions Hj has, the control to exclude the regions Hj from the subsequent processing may be conducted.

Thereafter, the control section 9a sets the region number j of the region Hj to j=1 to perform the processing which will be described hereinafter. The control section 9a uses a statistical discriminator based on the Bayes' theorem, discriminates which class the region Hj belongs to among four classes constituted of a gastric mucosa, villi, feces and bubbles, and performs classification based on the discrimination result.

More specifically, when in discrimination and classification of four classes, prior probability of one class ωa (a=1, 2, ..., C, C represents the number of classes) occurring is set as P(ωa), a feature vector determined from five feature values in the region Hj is set as x, a probability density function based on the probability of occurrence of the feature vector x from all the classes is set as p(x), and a state dependence probability density (multivariate normal probability density) function based on the probability of occurrence of the feature vector x from one class ωa is set as p(x|ωa), the calculation formula for calculating a posterior probability P (ωa|x) of the generating feature vector x belonging to one class ωa is expressed as the following formula (4).

$$P(\omega a|x) = p(x|\omega a)P(\omega a)/p(x) \quad (4)$$

The state dependence probability density function p(x|ωa) and the probability density function p(x) are expressed as the following formula (5) and formula (6).

$$p(\underline{x}|\omega a) = (1/((2\pi)^{d/2}|\Sigma a|^{1/2}))\exp\begin{bmatrix}(-1/2)(\underline{x}-\underline{\mu a})^t \\ \Sigma a^{-1}(\underline{x}-\underline{\mu a})\end{bmatrix} \quad (5)$$

$$p(\underline{x}) = \sum_{a=1}^{C} p(\underline{x}|\omega a)P(\omega a) \quad (6)$$

In the above described formula (5) and formula (6), d represents the number of dimensions which is the same as the number of feature values of x, and µa and Σa represent an average vector of the feature vectors x in the class ωa, and a variance-covariance matrix in one class ωa. Further, $(x-\mu a)^t$ represents the transposed matrix of (x–µa), and |Σa| represents a determinant of Σa, and $\Sigma a^{-1}$ represents an inverse matrix of Σa. Further, for simplification of the description, the prior probability P(ωa) is assumed to take an equal value in each of all the classes, and the probability density function p(x) is assumed to be expressed as a common function to all the classes by the above described formula (6).

The average vector µa and the variance covariance matrix Σa as the classification references are elements which configure population parameters in one class ωa, and are stored respectively in the terminal device 7 as the initial values after being calculated in advance for each of the classes from the feature vector x which is determined in each of one region of images based on a plurality of the images configuring the teacher data of the four classes constituted of a gastric mucosa, villi, feces and bubbles, in the stage before the first image I1 is inputted into the terminal device 7.

The average vector µa is constituted of the average values of the respective five feature values which the feature vector x has, and is a vector having the same number of dimensions as the feature vector x. More specifically, when the feature vector x is expressed as x=(x1, x2, x3, x4, x5), the average vector µa is expressed as µa=(µx1, µx2, µx3, µx4, µx5) by using µx1, µx2, µx3, µx4 and µx5 which are the average values of the respective five feature values which the feature vector x has. Further, the variance covariance matrix Σa is a matrix showing the variation and spread degree of the distribution of the feature vector x belonging to one class ωa, and is expressed as the matrix of d×d with respect to the number of dimensions d which is the same as the number of feature values of the feature vector x.

The control section 9a calculates the posterior probability P(ω1|x) that the generating feature vector x belongs to the class ω1, the posterior probability P(ω2|x) that the generating feature vector x belongs to the class ω2, the posterior probability P(ω3|x) that the generating feature vector x belongs to the class ω3, and the posterior probability P(ω4|x) that the generating feature vector x belongs to the class ω4, respectively by using the above described formula (4) to formula (6) based on the Bayes' theorem. The control section 9a performs discrimination by assuming that the feature vector x belongs to the class ωa which gives the maximum posterior probability P1 (ωa|x) among these four posterior probabilities, classifies the region Hj which is the region in which the feature vector x generates into the class ωa based on the discrimination result, and calculates the value of the probability density function p1(x|ωa) which gives the maximum posterior probability P1(ωa|x).

Subsequently, the control section 9a further performs processing based on the distance from the average value, namely, processing based on a threshold value with respect to the value of the probability density function p1(x|ωa) which gives the maximum posterior probability P1 (ωa|x), in order to determine whether the classification result of the region Hj classified into the class ωa in the processing up to the above is an accurate one or not.

More specifically, first, the control section 9a determines a threshold vector xb1 including a value obtained by adding the product of a standard deviation σx1 of the feature value x1 and a multiplication coefficient α as a predetermined constant to the average value μx1 of the feature value x1, for example, among the average value of each of the five feature values which the average vector μa has. Such a threshold vector xb1 is expressed as the following formula (7), for example, and in the present embodiment, the value of the multiplication coefficient α is set as 1.5.

$$xb1=(\mu x1+\alpha \times \sigma x1, \mu x2, \mu x3, \mu x4, \mu x5) \quad (7)$$

When the threshold vector xb1 is determined by the above described formula (7), the control section 9a substitutes the threshold vector xb1 as x of the above described formulas (4), (5) and (6), and calculates the value of the probability density function p(xb1|ωa) as the threshold value of the class ωa into which the region Hj is classified.

Subsequently, when the control section 9a detects that the value of p1(x|ωa) is larger than the value of p(xb1|ωa), the control section 9a determines that the classification result that the region Hj is classified into the class ωa is accurate.

Further, when the control section 9a detects that the value of p1(x|ωa) is the value of p(xb1|ωa) or less, the control section 9a determines that the classification result that the region Hj is classified into the class ωa is inaccurate, and classifies the region Hj into an unclear class.

Subsequently, the control section 9a performs the aforementioned series of processing for all $N^2/M^2$ of regions that are divided, and thereby, classifies the respective regions Hj into the non-biological mucosa class as the region group in which images of subjects such as feces and bubbles are picked up, for example, and the biological mucosa class as the region group in which images of subjects such as a gastric mucosa and villi are picked up.

Further, the control section 9a excludes each region which is classified as an unclear class among the respective regions Hj in the aforementioned processing from the target of processing described as follows. Further, the following description will be made with L ($L \leq N^2/M^2$) of regions Hsk ($1 \leq k \leq L$) out of $N^2/M^2$ of regions being assumed to be classified into the biological mucosa class by the aforementioned series of processing being performed and with the color tone feature values each of the regions Hsk has being set as μgsk and μbsk.

Thereafter, the control section 9a detects μgsk which is the color tone feature value which each of L of the regions Hsk classified into the biological mucosa class has (step S3 of FIG. 11). Further, the control section 9a as a color tone reference value calculating unit calculates the average value of the values of μgsk which the respective regions Hsk have as a color tone reference value MG_R (step S4 of FIG. 11).

More specifically, when μgsk is set as an axis of abscissa and μbsk is set as an axis of ordinates, respective data obtained by the processing of step S3 and step S4 of FIG. 11 are as schematically shown in FIG. 12, for example.

Next, the control section 9a as a lesion detection reference calculating unit calculates a threshold value thre1_i as the lesion detection reference in the image Ii, which is the threshold value relating to μgsk (for example, as thre1_i=0.3 when MG_R=0.55), based on the value of MG_R, and predetermined table data (or a predetermined function) shown as the graph of FIG. 13, for example (step S5 of FIG. 11). The threshold value thre1_i is not limited to the one calculated by using the aforementioned table data, but may be the one calculated based on a predetermined formula relating to the value of MG_R, for example.

Thereafter, the control section 9a performs processing which will be described hereinafter for each of regions Hs1, Hs2, ..., Hs(L−1), and HsL, and thereby, the control section 9a detects the regions in which the image of a bleeding site is picked up in the image Ii.

First, the control section 9a sets k=1 (step S6 of FIG. 11), and thereafter, detects whether or not the value of μgsk which is calculated in the region Hsk satisfies the relationship shown in the following formula (8).

$$\mu gsk < MG\_R - \text{thre}1\_i \quad (8)$$

Subsequently, when the control section 9a detects that the value of μgsk satisfies the relationship shown in the above described formula (8) (step S7 of FIG. 11), the control section 9a determines that the image of (at least either one of a redness or) a bleeding site as a lesion site showing a red color is picked up in the region Hsk (step S8 of FIG. 11). Further, when the control section 9a determines that the value of μgsk does not satisfy the relationship shown in the above described formula (8) (step S7 of FIG. 11), the control section 9a determines that the image of (both sites of a redness and) a bleeding site as the lesion site showing a red color is not picked up in the region Hsk (step S9 of FIG. 11).

When the control section 9a performs the processing of step S7, step S8 and Step S9 of FIG. 11 in the present embodiment, the control section 9a is assumed to make only determination based on the value of μgsk, and is not assumed to make determination based on the value of μbsk.

Further, in the present embodiment, the control section 9a is not limited to the one that makes determination based on the above described formula (8) when performing the processing of step S7, step S8 and step S9 of FIG. 11, but may calculate the ratio of the value of μgsk and the value of MG_R, for example, and may determine whether or not the image of a bleeding site is picked up in the region Hsk in accordance with the calculation result.

When the range of the value of μgsk which the region Hsk has in the processing of step S8 of FIG. 11, namely, the range of the value which is determined as the region in which the image of a bleeding site is picked up by the control section 9a is illustrated, the range becomes the range shown in FIG. 14. In other words, while each of the regions classified as the region in which the image of a biological mucosa is picked up shows the distribution of the value of μgsk which is relatively wide depending on the image pickup conditions, individual difference or the like, the region in which the image of a bleeding site is picked up among the each of the regions shows the distribution of the value of μgsk which is relatively narrow, since the image is picked up as the image having substantially the same color tone. The control section 9a can detect the region in which the image of a bleeding site is picked up in the respective regions which are classified as the regions where the image of a biological mucosa is picked up, based on the distribution of the value of μgsk as described above.

Thereafter, the control section 9a determines whether or not the processing shown from step S7 to step S9 of FIG. 11 is performed for all the L of regions in the image Ii. Subsequently, when the control section 9a detects that processing for all the L of regions is not performed (step S10 of FIG. 11), the control section sets k=k+1 (step S11 of FIG. 11), and thereafter, performs the processing from step S7 to step S10 of FIG. 11 again for the region Hs(k+1). Further, when the control section 9a detects that the processing for all the L of the regions is performed (step S10 of FIG. 11), the control section 9a finishes a series of processing for detecting the region in which the image of (at least either one of a redness or) a bleeding site is picked up in the image Ii.

The method for detecting the region in which the image of a bleeding site is picked up among the respective regions Hsk in the image Ii is not limited to the respective processing methods shown in step S7, step S8 and step S9 of FIG. 11, but may be a method by a discriminator using the Mahalanobis distance, which is configured based on the value of MG_R and the standard deviation of the value of μgsk which each of the regions Hsk has, for example. When the control section 9a detects the region in which the image of a bleeding site is picked up based on the method by the discriminator using the Mahalanobis distance, the control section 9a properly calculates the threshold value of the distance corresponding to the aforementioned threshold value thre1_i in accordance with the magnitude of the value of MG_R, and thereby, the control section 9a can obtain substantially the same operation as in the case of detecting the region in which the image of a bleeding site is picked up by using the aforementioned each processing.

Further, the control section 9a is not limited to the one using μgj(μgsk) as the color tone feature value, when performing each processing of the aforementioned calculation of the threshold value thre1_i, and determination of whether or not the image of a bleeding site is picked up, but may be the one that uses any one of, for example, the average value of giv/(riv+giv+biv), IHb (hemoglobin index) and the like.

Further, the value which is used as the color tone reference value in the aforementioned series of processing is not limited to the value of MG_R which is the average value of each of the values of μgsk, but may be any one of, for example, the average value of giv/riv calculated from the entire image Ii, the average value of the values of giv/riv calculated from the pixels other than the pixels of a dark portion, halation and the like in the image Ii, and the average value of each of μgj. Further, the value which is used as the color tone reference value in the aforementioned series of processing may be a difference value of the average value of the values of μgsk, and the standard deviation of the respective values of μgsk.

By performing a such series of processing described above as to change the threshold value used for processing for detecting a bleeding site (and a redness) as a lesion site showing a red color in accordance with the color tone of the biological mucosal surface, the terminal device 7 can precisely detect the bleeding site (and the redness). More specifically, even when a video signal of the image in which (at least one site of a redness and) a bleeding site is included on the surface of a normal biological mucosa tinged with red, for example, is inputted, the terminal device 7 can precisely detect the bleeding site (and the redness) by performing a series of processing shown in the flowchart of FIG. 11. As a result, a user can efficiently perform observation by the capsule type endoscope 3 when using the terminal device 7, as compared with the conventional image processing apparatus.

Each of the processing which is described above as the image processing operation of the present embodiment is not limited to the one that is applied to the image obtained at the time of observation by the capsule type endoscope, but may be the one that is applied to the image which is obtained at the time of observation by an endoscope or the like including, for example, an insertion section and an image pickup system.

(Second Embodiment)

Figure 15:
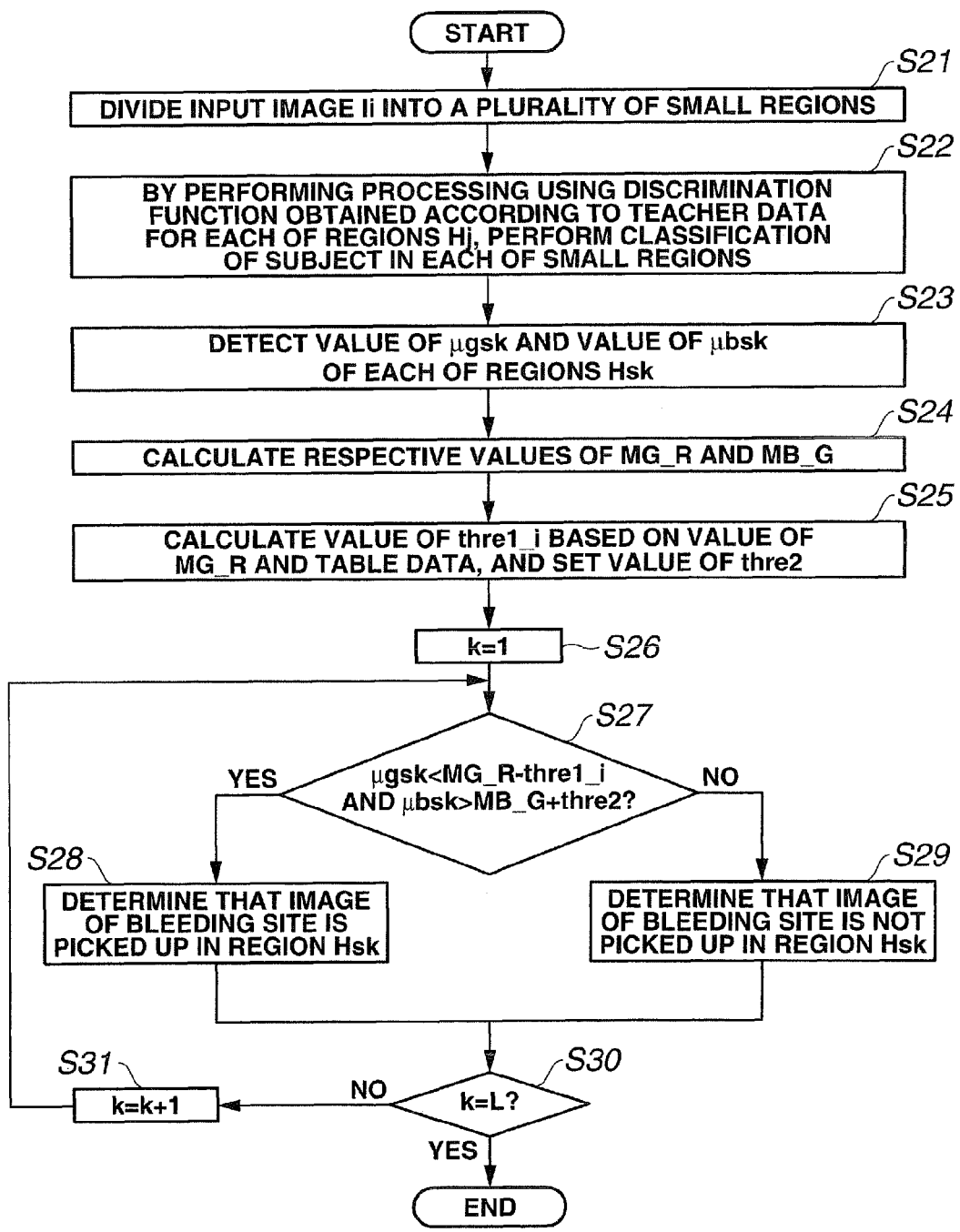
FIG. 15 is a flowchart showing one example of a procedure of processing carried out in a second embodiment by the medical image processing device of FIG. 1.
Figure 16:
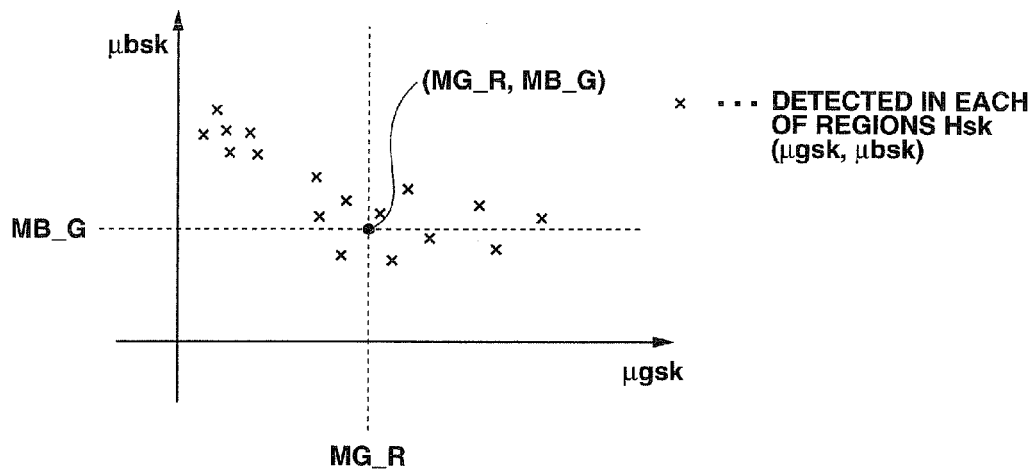
FIG. 16 is a schematic diagram of each data obtained when the processing of the flowchart of FIG. 15 is performed.
Figure 17:
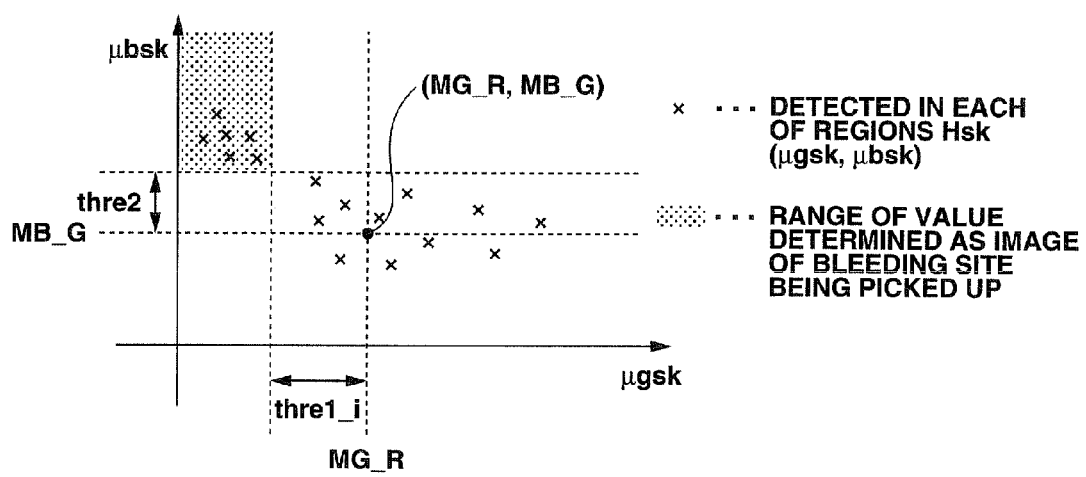
FIG. 17 is a diagram showing a range of a value which is determined as an image of a bleeding site being picked up in each data shown in FIG. 16.
Figure 18:
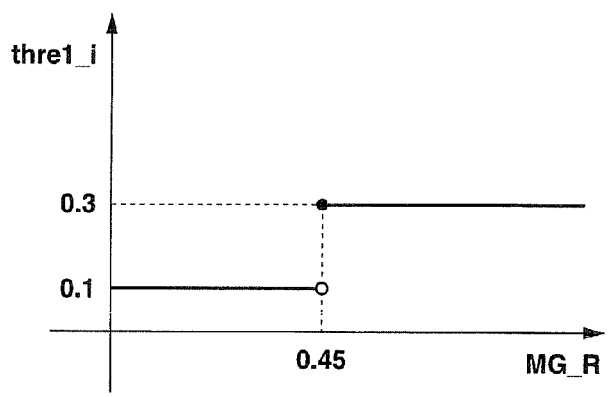
FIG. 18 is a diagram showing a different example from FIG. 13, of relationship between MG_R and thre1_i which are values used in the processing in the flowchart of FIG. 15.
Figure 19:
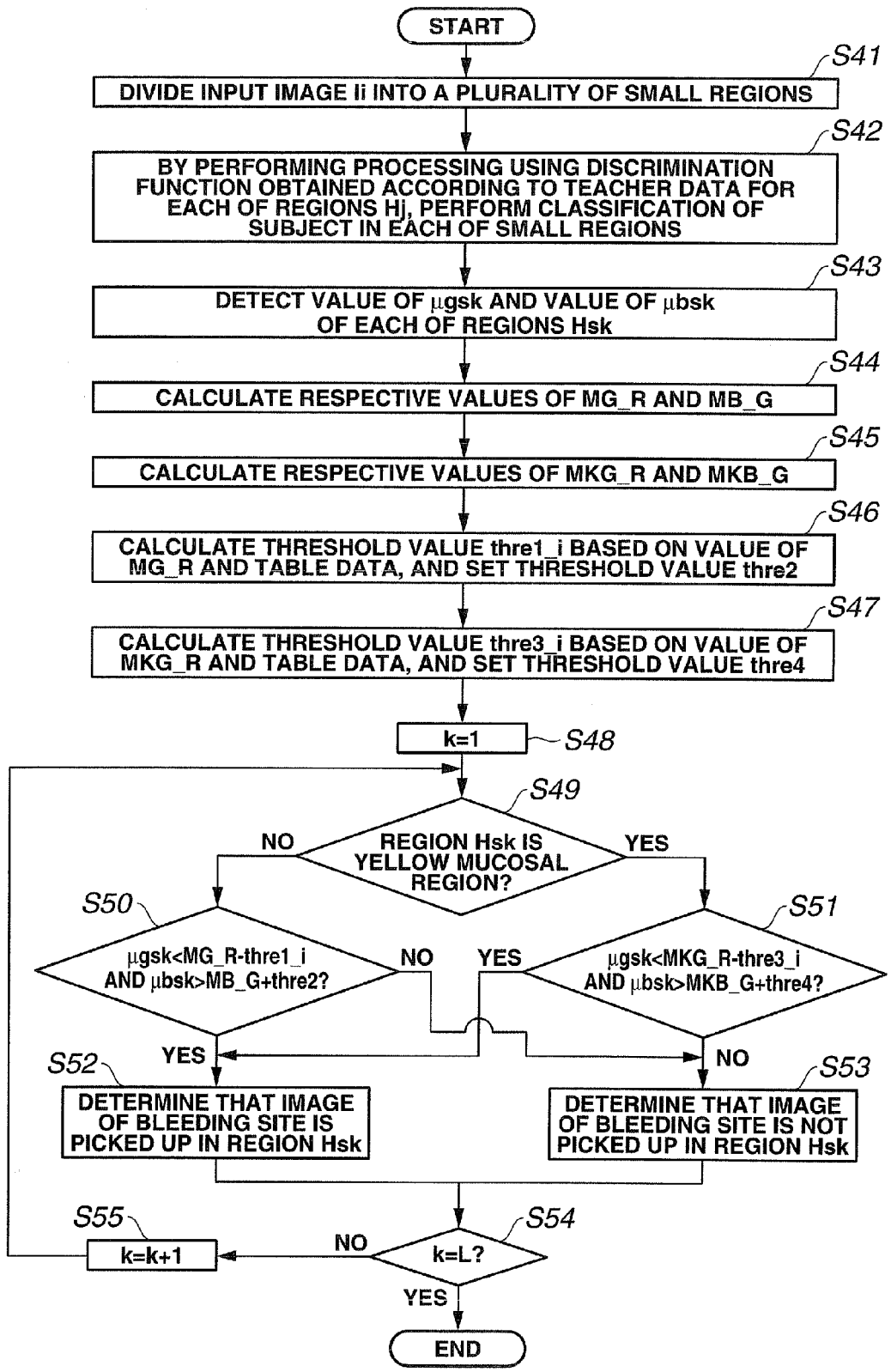
FIG. 19 is a flowchart showing a different example from FIG. 15, of a procedure of processing carried out in the second embodiment by the medical image processing device of FIG. 1.
Figure 20:
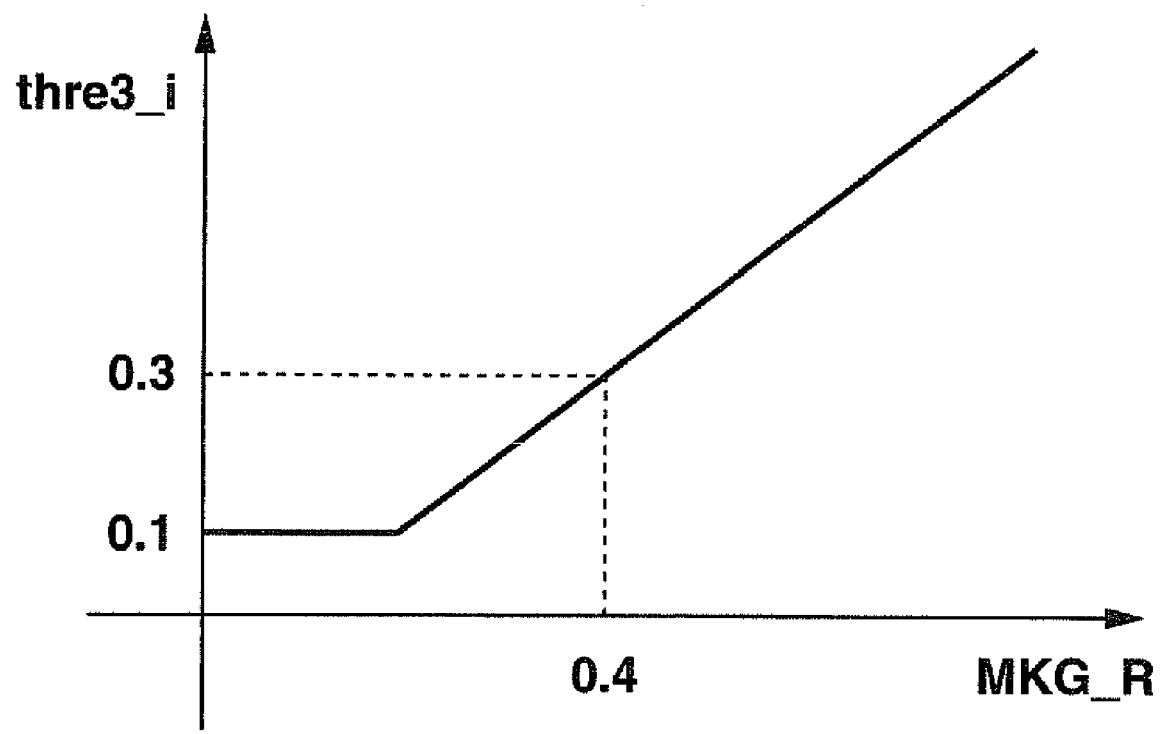
FIG. 20 is a diagram showing one example of relationship between MKG_R and thre3_i which are values used in the processing of the flowchart of FIG. 19.
Figure 21:
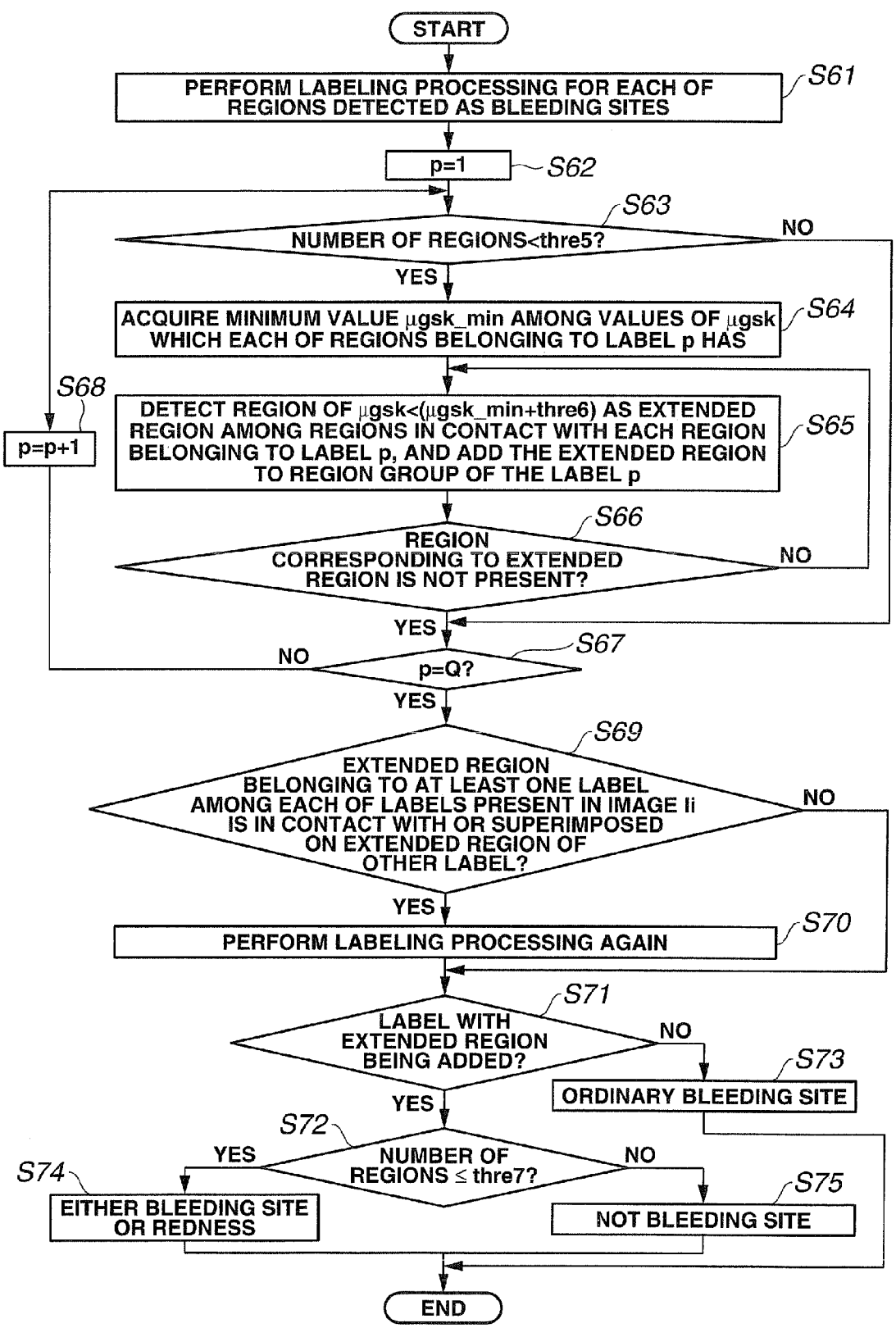
FIG. 21 is a diagram showing one example of processing which is performed by the medical image processing device of FIG. 1 subsequently to the flowchart of FIG. 15.
Figure 22:
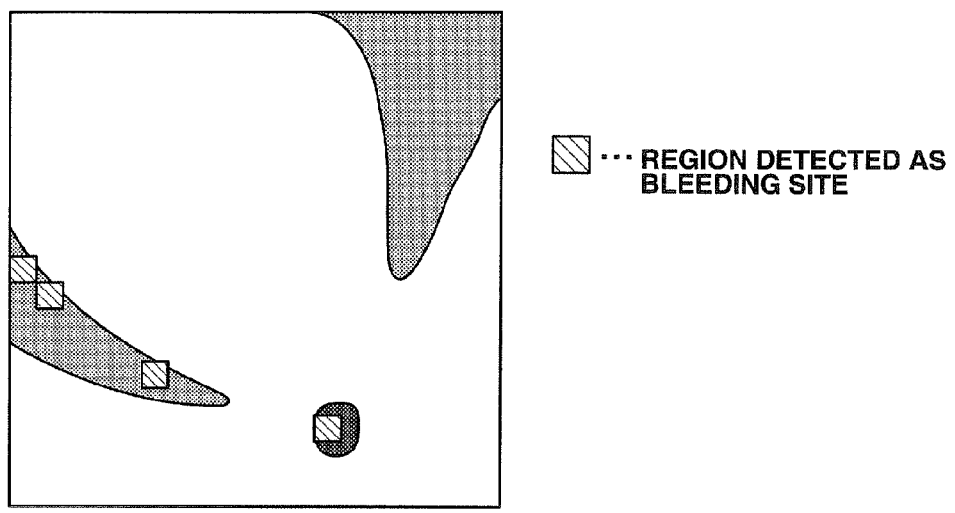
FIG. 22 is a view showing one example of a detection result of a bleeding site when the processing of the flowchart of FIG. 15 is performed.
Figure 23:
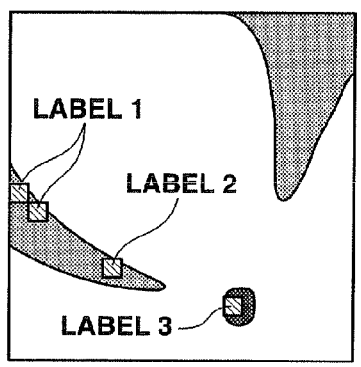
FIG. 23 is a view showing one example of a processing result when labeling processing is performed for the detection result of FIG. 22.
Figure 24:
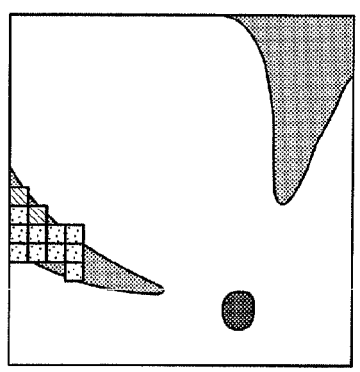
FIG. 24 is a view showing one example when a region shown as a label 1 of FIG. 23 is extended by processing based on the flowchart of FIG. 21.

Hereinafter, a second embodiment of the present invention will be described with reference to the drawings. FIGS. 15 to 28 relate to the second embodiment of the present invention. FIG. 15 is a flowchart showing one example of a procedure of processing which is carried out in the second embodiment by the medical image processing device of FIG. 1. FIG. 16 is a schematic diagram of each data obtained when the processing of the flowchart of FIG. 15 is performed. FIG. 17 is a diagram showing a range of a value which is determined as an image of a bleeding site being picked up, in each data shown in FIG. 16. FIG. 18 is a diagram showing a different example from FIG. 13, of relationship between MG_R and thre1_i which are values used in the processing of the flowchart of FIG. 15. FIG. 19 is a flowchart showing a different example from FIG. 15, of a procedure of processing which is carried out in the second embodiment by the medical image processing device of FIG. 1. FIG. 20 is a diagram showing one example of relationship between MKG_R and thre3_i which are values used in the processing of the flowchart of FIG. 19. FIG. 21 is a diagram showing one example of processing which is performed by the medical image processing device of FIG. 1 subsequently to the flowchart of FIG. 15. FIG. 22 is a view showing one example of a detection result of a bleeding site when the processing of the flowchart of FIG. 15 is performed. FIG. 23 is a view showing one example of a processing result when labeling processing is performed for the detection result of FIG. 22. FIG. 24 is a view showing one example when a region shown as a label 1 of FIG. 23 is extended by processing based on the flowchart of FIG. 21.

Figure 25:
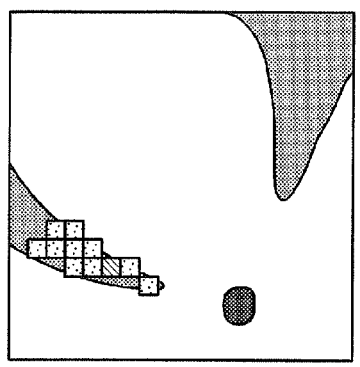
FIG. 25 is a view showing one example of the case in which a region shown as a label 2 of FIG. 23 is extended by the processing based on the flowchart of FIG. 21.
Figure 26:
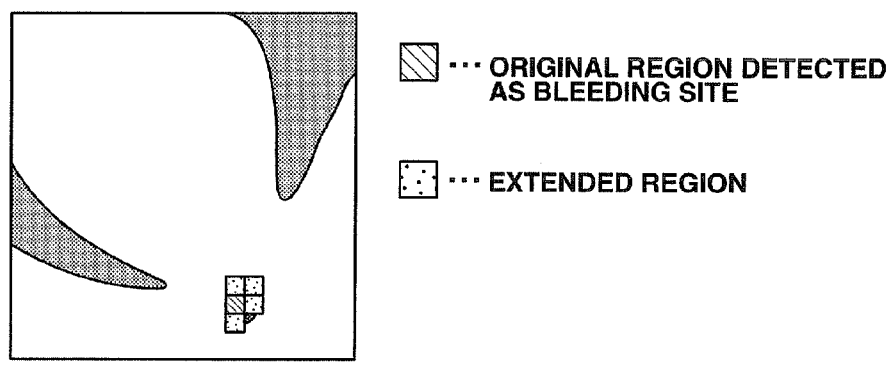
FIG. 26 is a view showing one example of the case in which a region shown as a label 3 of FIG. 23 is extended by the processing based on the flowchart of FIG. 21.
Figure 27:
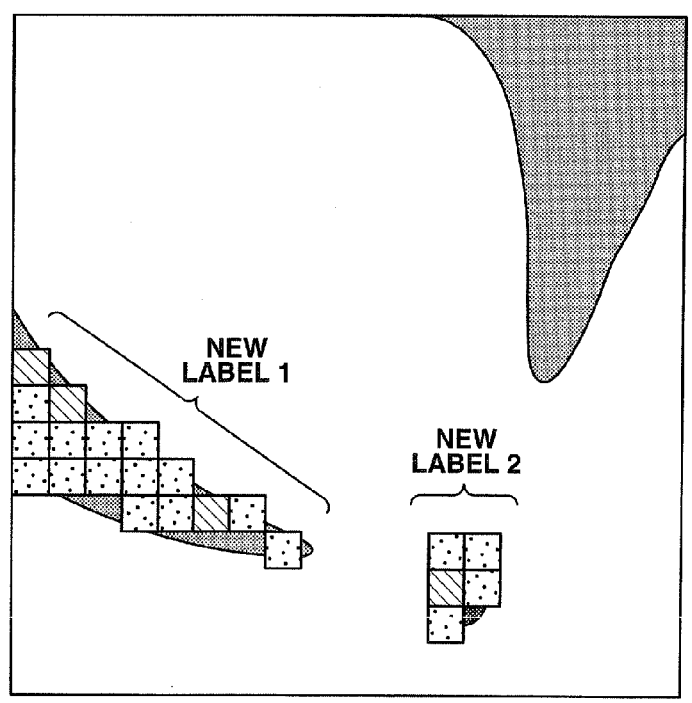
FIG. 27 is a view showing one example of a processing result of the case in which labeling processing is performed again in accordance with the extension result of each of the labels shown in FIG. 24 to FIG. 26.
Figure 28:
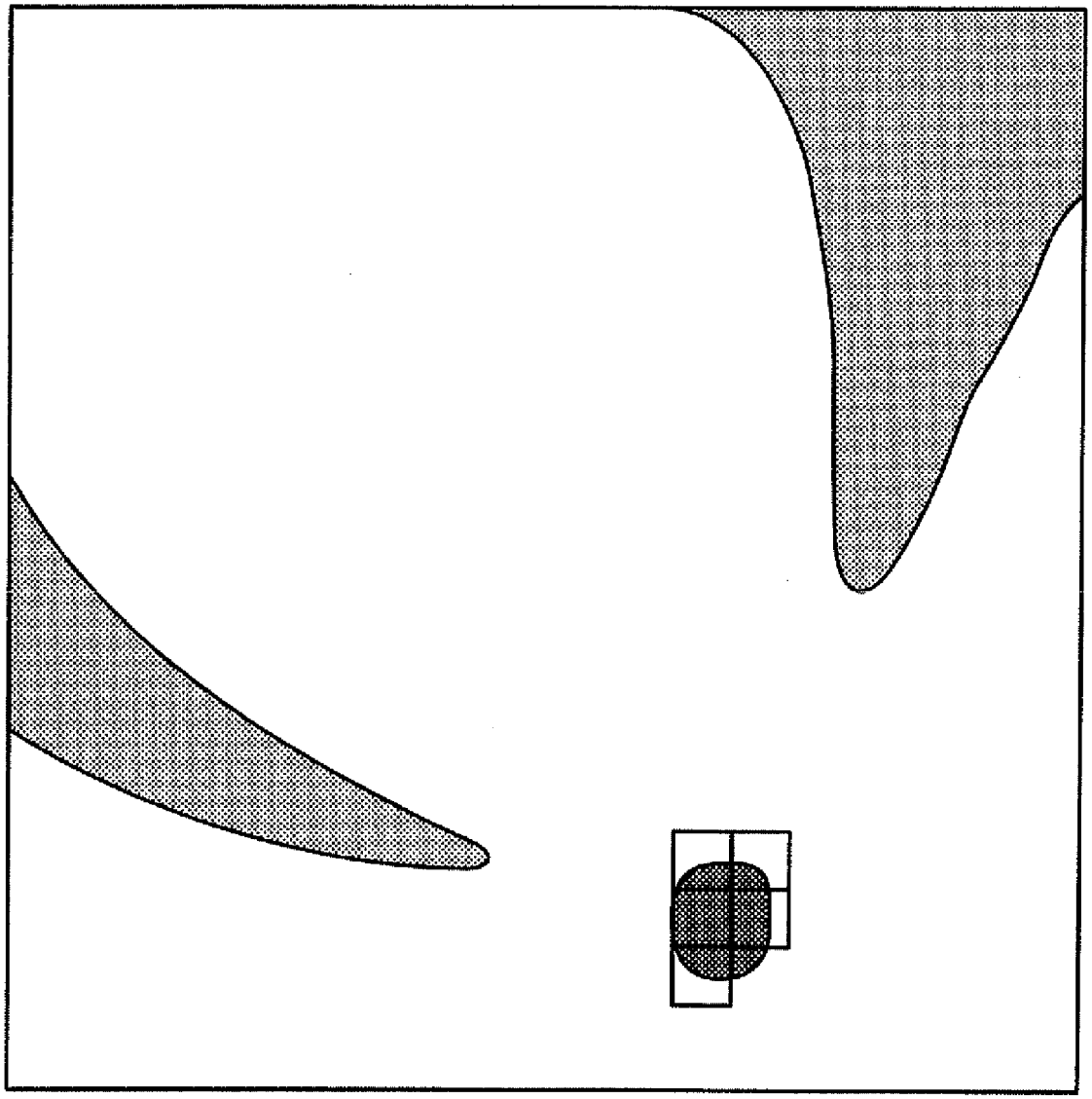
FIG. 28 is a view showing one example of a detection result of a bleeding site which is obtained when the processing of the flowchart of FIG. 21 is performed subsequently to the processing of the flowchart of FIG. 15.

Further, FIG. 25 is a view showing one example of the case in which a region shown as a label 2 of FIG. 23 is extended by processing based on the flowchart of FIG. 21. FIG. 26 is a view showing one example of the case in which a region shown as a label 3 of FIG. 23 is extended by processing based on the flowchart of FIG. 21. FIG. 27 is a view showing one example of a processing result of the case in which labeling processing is performed again in accordance with the extension result of each of the labels shown in FIG. 24 to FIG. 26. FIG. 28 is a view showing one example of a detection result of a bleeding site which is obtained when the processing of the flowchart of FIG. 21 is performed subsequently to the processing of the flowchart of FIG. 15.

The detailed description of the portions having the same configurations as in the first embodiment will be omitted. The same reference numerals and characters are used for the same components as in the first embodiment, and explanation of them will be omitted. Further, the configuration of the capsule type endoscope apparatus 1 used in the present embodiment is the same as the capsule type endoscope apparatus used in the first embodiment. Further, the image processing operation in the present embodiment is performed as the processing in the control section 9a which the terminal main body 9 has.

Next, an image processing operation of the present embodiment will be described.

First, the control section 9a as an image dividing unit and an image region classifying unit divides the image Ii having the size of N×N (number of pixels) into a plurality of rectangular regions each having a predetermined size, namely, ($N^2/M^2$) (a plurality) of small regions Hj ($1 \leq j \leq N^2/M^2$) each having the size of M×M (M<N) (step S21 of FIG. 15). Thereafter, the control section 9a performs processing using discriminating means such as a discriminant function based on the Bayesian discrimination rule, for example, which is obtained in accordance with teacher data for each of the regions Hj, and thereby, performs classification of the subject in each of the regions Hj (step S22 of FIG. 15).

For simplification of the description, the control section 9a performs the same processing as the processing shown in step S2 of FIG. 11 which is described above as the processing shown in step S22 of FIG. 15. More specifically, the control section 9a as the feature value calculating unit calculates each of values of μgj and μbj as the color tone feature value in the processing shown in step S22 of FIG. 15.

Further, the size of the image which is inputted into the control section 9a, and the size of the small region when the image is divided are not limited to the aforementioned sizes as long as they are the sizes to which the processing which will be described hereinafter is applicable, and for example, the size may be in a pixel unit (M=1).

Further, the following description will be made on the assumption that L (L≦N²/M²) of regions Hsk (1≦k≦L) out of N²/M² of regions are classified into the biological mucosa class by the aforementioned series of processing being performed, and the color tone feature values which each of the regions Hsk has are set as μgsk and μbsk.

Thereafter, the control section 9a detects μgsk and μbsk which are the color tone feature values which each of L of the regions Hsk which are classified into the biological mucosa class has (step S23 of FIG. 15). Further, the control section 9a as a color tone reference value calculating unit calculates the average value of the value of μgsk which each of the regions Hsk has as a color tone reference value MG_R, and calculates the average value of the value of μbsk which each of the regions Hsk has as a color tone reference value MB_G (step S24 of FIG. 15).

More specifically, when μgsk is set as an axis of abscissa and μbsk is set as an axis of ordinates, respective data obtained by processing of step S23 and step S24 of FIG. 15 are as schematically shown in FIG. 16, for example.

Next, the control section 9a as a lesion detection reference calculating unit calculates a threshold value thre1_i as the lesion detection reference in the image Ii, which is the threshold value relating to μgsk, based on the value of MG_R, and the predetermined table data shown as the graph of FIG. 13 which is described in the description of the first embodiment, for example, and sets the threshold value thre2 of μbsk (step S25 of FIG. 15). The threshold value thre2 is a predetermined value which does not depend on the value of MB_G. Further, the threshold value thre1_i is not limited to the one that is calculated by using the aforementioned table data, but may be the one that is calculated based on a predetermined formula relating to the value of MG_R, for example.

Thereafter, the control section 9a performs processing which will be described hereinafter for each of regions Hs1, Hs2, . . . , Hs (L−1), and HsL, and thereby, the control section 9a detects the region in which the image of a bleeding site is picked up in the image Ii.

First, the control section 9a sets k=1 (step S26 of FIG. 15), and thereafter, detects whether or not the values of μgsk and μbsk which are calculated in the region Hsk, satisfy the relationship expressed in the following formula (9) and formula (10).

$$\mu gsk < MG\_R - thre1\_i \quad (9)$$

$$\mu bsk > MB\_G + thre2 \quad (10)$$

Subsequently, when the control section 9a as an image region detecting unit detects that the value of μgsk satisfies the relationship expressed in the above described formula (9), and the value of μbsk satisfies the relationship expressed in the above described formula (10) (step S27 of FIG. 15), the control sections 9a determines that the image of (at least either one of a redness or) a bleeding site is picked up in the region Hsk (step S28 of FIG. 15). Further, when the control section 9a detects at least either one of that the value of μgsk does not satisfy the relationship expressed in the above described formula (9), or that the value of μbsk does not satisfy the relationship expressed in the above described formula (10) (step S27 of FIG. 15), the control section 9a determines that the image of (both sites of a redness and) a bleeding site is not picked up in the region Hsk (step S29 of FIG. 15).

When the range of the value of μgsk and the value of μbsk which the region Hsk has in the processing of step S28 of FIG. 15, namely, the range of the value which is determined as the region in which the image of a bleeding site is picked up by the control section 9a is illustrated, the range becomes the range shown in FIG. 17.

Thereafter, the control section 9a determines whether or not the processing shown in step S27 to step S29 of FIG. 15 is performed for all the L of regions in the image Ii. Subsequently, when the control section 9a detects that processing for all the L of regions is not performed (step S30 of FIG. 15), the control section 9a sets k=k+1 (step S31 of FIG. 15), and thereafter, performs the processing from step S27 to step S30 of FIG. 15 again for the region Hs(k+1). Further, when the control section 9a detects that the processing for all the L of the regions is performed (step S30 of FIG. 15), the control section 9a finishes a series of processing for detecting the region in which the image of (at least either one of a redness or) a bleeding site is picked up in the image Ii.

By performing such a series of processing described above as to change the threshold value used for processing for detecting a bleeding site (and a redness) in accordance with the color tone of the biological mucosal surface, the terminal device 7 can precisely detect the bleeding site (and the redness). More specifically, when a video signal of the image in which (at least one site of a redness and) a bleeding site is included on the surface of a normal biological mucosa tinged with red, for example, is inputted, the terminal device 7 can precisely detect the bleeding site (and the redness) by performing a series of processing shown in the flowchart of FIG. 15. As a result, a user can efficiently perform observation by the capsule type endoscope 3 when using the terminal device 7, as compared with the conventional device.

When M=1 is set in the processing shown in step S21 of FIG. 15, a series of processing shown in FIG. 15 is shown as the processing of determining whether or not the image of a bleeding site is picked up by the pixel unit. In this case, the terminal device 7 can further precisely detect the bleeding site in the image Ii as compared with the aforementioned processing of making determination for each region Hsk.

Further, in the processing shown in step S25 of FIG. 15, the table data used when the control section 9a calculates the value of thre1_i is not limited to the one that varies substantially linearly in accordance with the value of the color tone reference value MG_R as in the graph shown in FIG. 13, but may be the one that varies non-linearly. More specifically, for example, the table data which is used by the control section 9a when calculating thre1_i may the one in which the value of thre1_i in the case in which the value of MG_R is smaller than a predetermined threshold value (for example, 0.45) is 0.1, and the value of thre1_i in the case in which the value of MG_R is the predetermined threshold value or more is 0.3, as in the graph shown in FIG. 18.

Further, the value of thre2 set in the processing shown in step S25 of FIG. 15 is not limited to a predetermined value which does not depend on the value of MB_G, but may be the one that is calculated and set as the value in accordance with the value of MB_G by the table data different from the table data which is used when thre1_i is calculated, for example.

Further, the control section 9a is not limited to the one that makes determination based on the above described formula (9) and formula (10) in the processing shown in step S27 to step S29 of FIG. 15, but may be the one that makes determination based on the following formula (11) and formula (12), for example.

$$\log(\mu gsk) < \log(MG\_R) - \log(\text{thre1}\_i) \quad (11)$$

$$\log(\mu bsk) > \log(MB\_G) + \log(\text{thre2}) \quad (12)$$

Further, in the present embodiment, the control section 9a is not limited to the one that performs determination based on the value of MG_R and the value of MB_G. More specifically, the control section 9a may be the one that uses a threshold value thre11 relating to µgsk and a threshold value thre22 relating to µbsk, for example, and determines that the image of a bleeding site is picked up in the region Hsk irrespective of the respective values of MG_R and MB_G when the relationship of each of formulas of µgsk<thre11 and µbsk>thre22 is satisfied.

Further, the control section 9a may be the one that performs processing for classifying a region in which an image of a mucosal surface tinged with yellow due to bile or the like is picked up, namely, a yellow mucosal region as the region remarkably showing a yellow color tone, and a normal color mucosal region as a region in which a yellow color tone is suppressed, by further performing classification based on the color tone of each of the regions for each of the regions classified into the biological mucosa class in the processing shown in step S22 of FIG. 15, for example. In this case, the control section 9a performs the processing shown in the flowchart of FIG. 19 as will be described hereinafter, instead of the processing shown in the flowchart of FIG. 15.

First, the control section 9a as the image dividing unit and an image region classifying unit divides the image Ii into a plurality of small regions (step S41 of FIG. 19), and thereafter, the control section 9a performs processing with use of discriminating means such as a discriminant function based on, for example, the Bayesian discrimination rule, which is obtained in accordance with the teacher data, for each of the regions Hj, whereby the control section 9a performs classification of the subject in each of the regions Hj (step S42 of FIG. 19).

For simplification of the description, the control section 9a is assumed to be the one that performs the same processing as the processing shown in step S2 of FIG. 11 which is described above, as the processing shown in step S42 of FIG. 19. More specifically, the control section 9a as the feature value calculating unit is assumed to be the one that calculates the respective values of µgj and µbj as the color tone feature values in the processing shown in step S42 of FIG. 19.

Subsequently, by performing the aforementioned processing, the control section 9a classifies the respective regions Hj into, for example, the non-biological mucosa class as the region group in which the images of subjects such as feces and bubbles are picked up, and the biological mucosa class as the region group in which the images of subjects such as villi are picked up. Further, the control section 9a as the image region classifying unit further performs classification based on the color tone of each of the regions for each of the regions classified into the biological mucosa class, and thereby, makes classification of a region in which an image of a mucosal surface tinged with yellow due to bile or the like, namely, a yellow mucosal region as the region remarkably showing a yellow color tone, and a normal color mucosal region as a region in which a yellow color tone is suppressed. Subsequently, the control section 9a performs the subsequent processing while holding the aforementioned respective classification results.

Thereafter, the control section 9a detects µgsk and µbsk that are the color tone feature values which L of the regions Hsk classified into the biological mucosa group respectively have (step S43 of FIG. 19).

Further, the control section 9a as the color tone reference value calculating unit calculates the average value of the values of µgsk which the respective regions Hsk have as a color tone reference value MG_R, and calculates the average value of the values of µbsk which the respective regions Hsk have as the color tone reference value MB_G (step S44 of FIG. 19). Further, the control section 9a as the color tone reference value calculating unit calculates the average value of the values of µgsk which the regions classified as the yellow mucosal region have, among the respective regions Hsk which the image Ii has, as the color tone reference value MKG_R, and calculates the average value of the values of µbsk which the regions classified into the yellow mucosal region have as MKB_G (step S45 of FIG. 19).

Next, the control section 9a as a lesion detection reference calculating unit calculates the threshold value thre1_i as a lesion detection reference in the image Ii, which is the threshold value relating to µgsk based on the value of MG_R, and the table data shown as the graph of FIG. 13 which is described in the description of the first embodiment, for example, and sets the threshold value thre2 of µbsk (step S46 of FIG. 19). Further, the control section 9a as the lesion detection reference calculating unit calculates a threshold value thre3_i as a lesion detection reference in the image Ii, which is a threshold value relating to µgsk (in such a manner as thre3_i=0.3 when MKG_R=0.4, for example) based on the value of MKG_R and the table data shown as the graph of FIG. 20, for example, and sets a threshold value thre4 of µbsk (step S47 of FIG. 19). The value of thre2 is set as a predetermined value which does not depend on the value of MB_G, and the value of thre4 is set as a predetermined value which does not depend on the value of MKB_G.

Thereafter, the control section 9a performs the processing which will be described hereinafter for each of the regions Hs1, Hs2, ..., Hs(L−1), and HsL, and thereby, detects the region in which the image of a bleeding site is picked up in the image Ii.

First, after the control section 9a sets k=1 (step S48 of FIG. 19), the control section 9a detects whether the region Hsk is the region which is classified into the yellow mucosal region, or the region which is classified into the normal color mucosal region.

When the control section 9a detects that the region Hsk is the region classified into the normal color mucosal region (step S49 of FIG. 19), the control section 9a further detects whether the value of µgsk and the value of µbsk which the region Hsk has satisfy both the relationships expressed in the above described formula (9) and formula (10).

When the control section 9a as the image region detecting unit detects that the value of µgsk, which the region Hsk classified into the normal color mucosal region has, satisfies the relationship expressed in the above described formula (9), and that the value of µbsk, which the region Hsk classified into the normal color mucosal region has, satisfies the relationship expressed in the above described formula (10) (step S50 of FIG. 19), the control section 9a determines that the image of (at least either one of a redness or) a bleeding site is picked up in the region Hsk (step S52 of FIG. 19). Further, when the control section 9a detects at least either one of the fact that the value of µgsk does not satisfy the relationship expressed in the above described formula (9), or the fact that the value of µbsk does not satisfy the relationship expressed in formula (10) (step S50 of FIG. 19), the control section 9a determines that the image of (both sites of a redness and) a bleeding site is not picked up in the region Hsk (step S53 of FIG. 19).

Meanwhile, when the control section 9a detects that the region Hsk is the region which is classified into the yellow mucosal region (step S49 of FIG. 19), the control section 9a further detects whether or not the value of μgsk and the value of μbsk which the region Hsk has satisfy both the relationships expressed in the following formula (13) and formula (14).

$$\mu gsk < MKG\_R - thre3\_i \tag{13}$$

$$\mu bsk > MKB\_G + thre4 \tag{14}$$

When the control section 9a as the image region detecting unit detects that the value of μgsk, which the region Hsk classified into the yellow mucosal region has, satisfies the relationship expressed in the above described formula (13), and that the value of μbsk, which the region Hsk classified into the yellow mucosal region has, satisfies the relationship expressed in formula (14) (step S51 of FIG. 19), the control section 9a determines that the image of (at least either one of a redness or) a bleeding site is picked up in the region Hsk (step S52 of FIG. 19). Further, when the control section 9a detects at least either one of the fact that the value of μgsk does not satisfy the relationship expressed in the above described formula (13), or the fact that the value of μbsk does not satisfy the relationship expressed in formula (14) (step S51 of FIG. 19), the control section 9a determines that the image of (both sites of a redness and) a bleeding site is not picked up in the region Hsk (step S53 of FIG. 19).

Thereafter, the control section 9a determines whether or not the processing shown in step S49 to step S53 of FIG. 19 is performed for all of L of the regions in the image Ii. When the control section 9a detects that the processing for all L of the regions is not performed (step S54 of FIG. 19), the control section 9a sets k=k+1 (step S55 of FIG. 19), and thereafter, the control section 9a performs the processing from step S49 to step S54 of FIG. 19 again for the region Hs(k+1). Further, when the control section 9a detects that the processing for all L of the regions is performed (step S54 of FIG. 19), the control section 9a finishes a series of processing for detecting the regions in which the image of (at least either one of a redness or) a bleeding site is picked up in the image Ii which is described above.

When a video signal of the image in which (at least one site of a redness and) a bleeding site is included in the surface of a normal biological mucosa tinged with yellow by being covered with bile or the like, for example, is inputted, the terminal device 7 can obtain the effect of being capable of precisely detecting the bleeding site (and the redness) by performing a series of processing shown in the flowchart of FIG. 19, in addition to the effect of the case in which the processing shown in the flowchart of FIG. 15 is performed.

A series of processing shown in FIG. 19 may be the one that is performed as the processing of determining whether or not the image of a bleeding site is picked up for each pixel as a series of processing shown in FIG. 15. In this case, the terminal device 7 can more precisely detect a bleeding site in the image Ii as compared with the processing of determination for each region Hsk as described above.

Further, in the processing shown in step S47 of FIG. 19, the table data used when the control section 9a calculates thre3_i is not limited to the one that varies substantially linearly in accordance with the value of MKG_R as the graph shown in FIG. 20, but may be the one that varies non-linearly.

Further, the value of thre4 which is set in the processing shown in step S47 of FIG. 19 of the present embodiment is not limited to a predetermined value which does not depend on the value of MKB_G, but may be the value which is calculated and set as the value in accordance with the value of MKB_G by table data different from the table data which is used when, for example, thre1_i and thre3_i are calculated.

Further, the control section 9a is not limited to the one that makes determination based on the above described formula (9) and formula (10) in the processing shown in steps S50, S52 and S53 of FIG. 19, but may the one that makes determination based on the above described formula (11) and formula (12). Further, the control section 9a is not limited to the one that performs determination based on the above described formula (13) and formula (14) in the processing shown in steps S51, S52 and S53 of FIG. 19, but may be the one that makes determination based on the above described formula (15) and formula (16).

$$\log(\mu gsk) < \log(MKG\_R) - \log(thre3\_i) \tag{15}$$

$$\log(\mu bsk) > \log(MKB\_G) + \log(thre4) \tag{16}$$

Further, the control section 9a of the capsule type endoscope 1 may be the one that performs processing shown in the flowchart of FIG. 21 as will be described hereinafter, in addition to the processing shown in FIG. 15.

Hereinafter, description will be made on the assumption that the detection result of the bleeding site in the image Ii as shown in FIG. 22, and each data (μgsk, μbsk and the like) which is required for detecting the bleeding site are already obtained by performing the processing shown in the flowchart of FIG. 15 before the processing shown in the flowchart of FIG. 21 is performed. Further, hereinafter, description will be made on the assumption that the processing shown in the flowchart of FIG. 15 is performed with M=8 being set.

The control section 9a performs labeling processing for dealing the regions close to each other as the regions which belong to the same region group by assigning the respective regions, which are detected as bleeding sites based on the detection result of the bleeding site in the image Ii, with numbers or the like (step S61 of FIG. 21). More specifically, as the labeling processing shown in step S61 of FIG. 21, when in an adjacent 8 regions to one region detected as a bleeding site, another region detected as a bleeding site is present as shown in FIG. 23, for example, the control section 9a performs processing for dealing the one region and the other region as the regions which belong to a label p (p=1, 2 . . . , Q−1, Q) which is the same region group. FIG. 23 is a view showing an example in which Q=3, two regions belong to a label 1, one region belongs to a label 2, and one region belongs to a label 3.

Thereafter, after the control section 9a sets p=1 (step S62 of FIG. 21), the control section 9a determines whether or not the number of regions which the label p has is smaller than the threshold value thre5. The threshold value thre5 is a threshold value which depends on the value of M used in the processing shown in the flowchart of FIG. 15, is a threshold value relating to the number of regions that the label p has, and is a value set as thre5=5 (region) in the present embodiment, for example.

When the control section 9a detects that the number of regions that the label p has is the threshold value thre5 or more (step S63 of FIG. 21), the control section 9a performs the processing shown in step S67 of FIG. 21 which will be described later. Further, when the control section 9a detects that the number of regions that the label p has is smaller than the threshold value thre5 (step S63 of FIG. 21), the control section 9a acquires the minimum value μgsk_min among the values of µgsk which the respective regions belonging to the label p have (step S64 of FIG. 21).

Further, the control section 9a as a target region extending unit performs processing of detecting a region which is present in the vicinity of each of the regions belonging to the label p and has the color tone analogous to that of each of the regions. More specifically, the control section 9a detects the region satisfying µgsk<(µgsk_min+thre6) of the regions in contact with each of the regions belonging to the label p as an extension region, and adds the extension region to the region group of the label p (step S65 of FIG. 21). The threshold value thre6 is a threshold value relating to each of the values of µgsk and µgsk_min, and is the value which is set as thre6=0.1 in the present embodiment, for example.

The control section 9a repeatedly performs the processing shown in step S65 of FIG. 21 until the region corresponding to the aforementioned extension region is not detected (step S66 of FIG. 21). Further, when the extension region belonging to the label p is not detected, the control section 9a determines whether or not the control section 9a performs the processing shown in step S63 to step S65 of FIG. 21 for all Q of labels.

When the control section 9a detects that the processing for all Q of the labels is not performed (step S67 of FIG. 21), the control section 9a sets p=p+1 (step S68 of FIG. 21), and thereafter, the control section performs the processing from step S63 to step S67 of FIG. 21 again for a label (p+1). Further, when the control section 9a detects that the processing for all Q of labels is performed (step S67 of FIG. 21), the control section 9a performs the processing shown in step S69 of FIG. 21 which will be described later.

More specifically, when the control section 9a performs the processing shown in step S62 to step S68 of FIG. 21 for each of the labels in the state as shown in FIG. 23, for example, the control section 9 extends the label 1 as the region group as shown in FIG. 24, extends the label 2 as the region group as shown in FIG. 25, and extends the label 3 as the region group as shown in FIG. 26.

Further, the control section 9a as the target region extending unit performs the processing of detecting another label which a region existing in the vicinity of each of the regions belonging to one label and having the color tone analogous to each of the regions belongs to. More specifically, the control section 9a performs processing of determining whether the extension region belonging to one label is in contact with the extension region of another label or not, or is superimposed on the extension region of another label or not for each of the labels present in the image Ii. When the control section 9a detects that the extension region belonging to one label and the extension region belonging to another label are not in contact with each other and are not superimposed on each other in each of the labels present in the image Ii (step S69 of FIG. 21), the control section 9a determines that the color tones of the one label and the other label are not analogous to each other, and performs the processing shown in step S71 of FIG. 21 which will be described later. Further, when the control section 9a detects at least either one of the sate in which the extension region belonging to at least one label of all the labels present in the image Ii is in contact with the extension region of the other label, or the state in which it is superimposed on the extension region of the other label (step S69 of FIG. 21), the control section 9a determines that the color tones of the one label and the other label are analogous to each other, and performs labeling processing again (step S70 of FIG. 21).

When the control section 9a detects that six regions superimposed on each other in the label 1 having 12 regions including the extension region and the label 2 having 11 regions including the extension region, the control section 9a determines that the color tones of the label 1 and the label 2 are analogous to each other, and performs processing for dealing the region group having 17 regions from which the superimposition of the six regions is excluded as a new label 1, for example, as shown in FIGS. 24, 25 and 27, as the processing included in the labeling processing shown in step S70 of FIG. 21. Further, the control section 9a performs processing for dealing the region group which is originally dealt as the label 3 as a new label 2 this time, after the aforementioned new label 1 is generated, for example, as shown in FIGS. 26 and 27, as the processing included in the labeling processing shown in step S70 of FIG. 21.

In other words, when the control section 9a detects any one state of the state in which the extension region belonging to one label is in contact with the extension region of the other label, and the state in which the extension region belonging to one label is superimposed on the extension region of the other label, the control section 9a performs processing of dealing the one label and the other label as the region belonging to the label q (q=1, 2, . . . , T−1, T) which is the same label as the processing included in the labeling processing shown in step S70 of FIG. 21.

After the processing of step S69 or the processing of step S70 of FIG. 21 is performed, the control section 9a performs processing for identifying which label is the label having the extension region added by the processing from step S64 to step S66 of FIG. 21, and which label is the label which does not have the extension region, among all the labels remaining in the image Ii.

Thereafter, the control section 9a detects each of the labels identified by the aforementioned processing, which does not have the extension region, as the region in which an ordinary (area) bleeding site is present, and finishes a series of processing in the image Ii described above (step S71 and step S73 of FIG. 21). Further, the control section 9a as the target region determining unit determines whether or not the number of regions which each of the labels has is the threshold value thre7 or less for each of the labels having the extension region which are identified by the aforementioned processing (step S71 and step S72 of FIG. 21). The threshold value thre7 is a threshold value which depends on the value of M used in the processing shown in the flowchart of FIG. 15, and relates to the number of regions which the aforementioned each of the labels has, and is the value which is set as thre7=15 (region) in the present embodiment, for example.

The control section 9a detects each of the labels with the number of regions being the threshold value thre7 or less as the region group in which the image of at least either one of a bleeding site (with a smaller area as compared with an ordinary one), or a redness is picked up, and finishes a series of processing in the image Ii described above (step S72 and step S74 of FIG. 21). Further, the control section 9a detects each label with the number of regions being larger than the threshold value thre7 as the region group in which, for example, a fold, a crena or the like is present as the subject different from a bleeding site, and excludes the region group which each of the label has from the detection result of the bleeding site by the processing shown in the flowchart of FIG. 15. Thereafter, the control section 9a finishes the series of processing in the image Ii described above (step S72 and step S75 of FIG. 21).

More specifically, by performing the processing shown in step S71 to step S75 shown in FIG. 21 for the new label 1 shown in FIG. 27, the control section 9a excludes the 17 regions, which the new label 1 in which the extension region is added has, from the detection result of the bleeding site by the processing shown in the flowchart of FIG. 15 as the region group in which the subject differing from the bleeding site is present. Further, by performing the processing from step S71 to step S75 shown in FIG. 21 for the new label 2 shown in FIG. 27, the control section 9a detects five regions, which the new label 2 in which the extension region is added has, as the region group in which the image of at least either one of a bleeding site (with a smaller area as compared with an ordinary bleeding site) or a redness is picked up. Subsequently, the control section 9a obtains the detection result as shown in FIG. 28 as the final detection result.

Even when the processing shown in the flowchart of FIG. 15 is performed in the state with M=1 is set, the processing shown in the flowchart of FIG. 21 can be applied by properly changing the values of the threshold values thre5 and thre7 (in accordance with the value of M).

Further, the control section 9a may perform determination based on the value of µgsk which each of the regions belonging to one label has in the processing shown in steps S72, S74 and S75 of FIG. 21.

More specifically, in the processing shown in steps S72, S74 and S75 of FIG. 21, based on whether or not the minimum value is present in the distribution of the value of µgsk of each of the regions belonging to one label, when the minimum value is present, the control section 9a may determine that each of the regions is the region in which the image of at least either one of a bleeding site (with a smaller area as compared with the ordinary site) or a redness is picked up. When the minimum value is not present, the control section 9a may determine that each of the regions is a region in which a subject different from a bleeding site is present.

Further, in the processing shown in steps S72, S74 and S75 of FIG. 21, the control section 9a calculates the average value of the values of µgsk which the respective regions belonging to one label have, and when the average value is a predetermined value or less, the control section 9a may determine that each of the regions is the region in which the image of at least either one of a bleeding site (with a smaller area as compared with the ordinary site) or a redness is picked up, and when the average value is larger than the predetermined value, the control section 9a may determine that each of the regions is the region in which a subject different from a bleeding site is present.

Even when a video signal having the image of (at least one site of either a redness or) a bleeding site with a smaller area as compared with an ordinary bleeding site, for example, is inputted, the terminal device 7 can obtain the effect of being capable of precisely detecting that the bleeding site (and the redness) by performing a series of processing shown in the flowchart of FIG. 21, in addition to the effect of the case of performing the processing shown in the flowchart of FIG. 15.

Each of the processing described above as the image processing operation of the present embodiment is not limited to the one which is applied to the image obtained at the time of observation by a capsule type endoscope, but may be applied to the image which is obtained at the time of observation by an endoscope or the like including, for example, an insertion section and an image pickup system.

Further, the present invention is not limited to the above described each of the embodiments, but various changes and applications can be made in the range without departing from the spirit of the invention.

What is claimed is:

1. A medical image processing device, comprising:
   an image dividing unit which divides an image corresponding to a subject image which is picked up by a medical image pickup apparatus into a plurality of regions constituted of at least one or more pixels;
   a feature value calculating unit which calculates a color tone feature value which is a feature value based on a color tone of the image in each of the plurality of regions;
   a first image region classifying unit which classifies each of regions in which an image of a biological mucosa is picked up as the subject among the plurality of regions as a biological mucosa class;
   a first color tone reference value calculating unit which calculates a first color tone reference value based on the color tone feature value which each of the plurality of regions has;
   a first lesion detection reference calculating unit which properly calculates a first lesion detection reference for detecting at least either one of a bleeding site or a redness in accordance with the first color tone reference value;
   a first image region detecting unit which detects a first target region that is a region in which an image of at least either one of a bleeding site or a redness is picked up among the respective plurality of regions, based on the first lesion detection reference and the color tone feature value which each of the plurality of regions has;
   a second image region classifying unit which classifies a region in which a yellow color tone is remarkably shown as a yellow mucosal region, among each of the regions classified into the biological mucosa class, based on a classification result of the first image region classifying unit;
   a second color tone reference value calculating unit which calculates a second color tone reference value based on the color tone feature value which each of the regions classified as the yellow mucosal region has;
   a second lesion detection reference calculating unit which calculates a second lesion detection reference in each of the regions classified as the yellow mucosal region in accordance with the second color tone reference value; and
   a second image region detecting unit which detects a second target region which is a region in which an image of at least either one of a bleeding site or a redness is picked up, among each of the regions classified as the yellow mucosal region, based on the second lesion detection reference, and the color tone feature value which each of the regions classified as the yellow mucosal region has.

2. The medical image processing device according to claim 1, wherein the first lesion detection reference calculating unit properly calculates the first lesion detection reference based on predetermined table data relating to the first color tone reference value.

3. The medical image processing device according to claim 2, wherein the image dividing unit divides the image into a plurality of rectangular regions having a predetermined number of pixels.

4. The medical image processing device according to claim 2, wherein the image dividing unit divides the image by a pixel unit.

5. The medical image processing device according to claim 1, wherein the first lesion detection reference calculating unit properly calculates the first lesion detection reference by using a predetermined function corresponding to the first color tone reference value.

6. The medical image processing device according to claim 5, wherein the image dividing unit divides the image into a plurality of rectangular regions having a predetermined number of pixels.

7. The medical image processing device according to claim 5, wherein the image dividing unit divides the image by a pixel unit.

8. The medical image processing device according to claim 1, wherein the first lesion detection reference calculating unit properly calculates the first lesion detection reference based on a discriminator configured in correspondence with the first color tone reference value.

9. The medical image processing device according to claim 8, wherein the image dividing unit divides the image into a plurality of rectangular regions having a predetermined number of pixels.

10. The medical image processing device according to claim 8, wherein the image dividing unit divides the image by a pixel unit.

11. The medical image processing device according to claim 1, wherein the image dividing unit divides the image into a plurality of rectangular regions having a predetermined number of pixels.

12. The medical image processing device according to claim 1, wherein the image dividing unit divides the image by a pixel unit.

13. The medical image processing device according to claim 1, further comprising:
a target region extending unit which sets one target region group by combining each of regions which is present in a vicinity of the first target region and has a color tone analogous to the color tone of the first target region among each of the regions classified as the biological mucosa class, to the first target region, based on the color tone feature value which the first target region has; and
a target region determining unit which determines whether the one target region group is a region group in which an image of at least either one of a bleeding site or a redness is picked up or not based on a number of regions which the one target region group has.

14. The medical image processing device according to claim 1, further comprising:
a target region extending unit which sets one target region group by combining each of regions which is present in a vicinity of the first target region and has a color tone analogous to the color tone of the first target region among each of the regions classified as the biological mucosa class, to the first target region, based on the color tone feature value which the first target region has; and
a target region determining unit which determines whether the one target region group is a region group in which an image of at least either one of a bleeding site or a redness is picked up or not based on the average value of the color tone feature value which the one target region group has.

15. A medical image processing device comprising:
an image dividing unit which divides an image corresponding to a subject image which is picked up by a medical image pickup apparatus into a plurality of regions constituted of at least one or more pixels;
a feature value calculating unit which calculates a color tone feature value which is a feature value based on a color tone of the image in each of the plurality of regions;
a first image region classifying unit which classifies each of regions in which an image of a biological mucosa is picked up as the subject among the plurality of regions as a biological mucosa class;
a first color tone reference value calculating unit which calculates a first color tone reference value which is an average value of the color tone feature value which each of the regions classified as the biological mucosa class has, based on the color tone feature value which each of the plurality of regions has;
a first lesion detection reference calculating unit which properly calculates a first lesion detection reference for detecting at least either one of a bleeding site or a redness in accordance with the first color tone reference value;
a first image region detecting unit which detects a first target region that is a region in which an image of at least either one of a bleeding site or a redness is picked up among the respective plurality of regions, based on the first lesion detection reference and the color tone feature value which each of the plurality of regions has;
a second image region classifying unit which classifies a region in which a yellow color tone is remarkably shown as a yellow mucosal region, among each of the regions classified into the biological mucosa class based on a classification result of the first image region classifying unit;
a second color tone reference value calculating unit which calculates a second color tone reference value based on the color tone feature value which each of the regions classified as the yellow mucosal region has;
a second lesion detection reference calculating unit which calculates a second lesion detection reference in each of the regions classified as the yellow mucosal region in accordance with the second color tone reference value; and
a second image region detecting unit which detects a second target region which is a region in which an image of at least either one of a bleeding site or a redness is picked up, among each of the regions classified as the yellow mucosal region, based on the second lesion detection reference, and the color tone feature value which each of the regions classified as the yellow mucosal region has.

16. The medical image processing device according to claim 15, wherein the first lesion detection reference calculating unit properly calculates the first lesion detection reference based on predetermined table data relating to the first color tone reference value.

17. The medical image processing device according to claim 16, wherein the image dividing unit divides the image into a plurality of rectangular regions having a predetermined number of pixels.

18. The medical image processing device according to claim 16, wherein the image dividing unit divides the image by a pixel unit.

19. The medical image processing device according to claim 15, wherein the first lesion detection reference calculating unit properly calculates the first lesion detection reference by using a predetermined function corresponding to the first color tone reference value.

20. The medical image processing device according to claim 19, wherein the image dividing unit divides the image into a plurality of rectangular regions having a predetermined number of pixels.

21. The medical image processing device according to claim 19, wherein the image dividing unit divides the image by a pixel unit.

22. The medical image processing device according to claim 15, wherein the first lesion detection reference calculating unit properly calculates the first lesion detection reference based on a discriminator configured in correspondence with the first color tone reference value.

23. The medical image processing device according to claim 22, wherein the image dividing unit divides the image into a plurality of rectangular regions having a predetermined number of pixels.

24. The medical image processing device according to claim 22 wherein the image dividing unit divides the image by a pixel unit.

25. The medical image processing device according to claim 15, wherein the image dividing unit divides the image into a plurality of rectangular regions having a predetermined number of pixels.

26. The medical image processing device according to claim 15, wherein the image dividing unit divides the image by a pixel unit.

27. The medical image processing device according to claim 15, further comprising:
a target region extending unit which sets one target region group by combining each of regions which is present in a vicinity of the first target region and has a color tone analogous to the color tone of the first target region among each of the regions classified as the biological mucosa class, to the first target region, based on the color tone feature value which the first target region has; and
a target region determining unit which determines whether the one target region group is a region group in which an image of at least either one of a bleeding site or a redness is picked up or not based on a number of regions which the one target region group has.

28. The medical image processing device according to claim 15, further comprising:
a target region extending unit which sets one target region group by combining each of regions which is present in a vicinity of the first target region and has a color tone analogous to the color tone of the first target region among each of the regions classified as the biological mucosa class, to the first target region, based on the color tone feature value which the first target region has; and
a target region determining unit which determines whether the one target region group is a region group in which an image of at least either one of a bleeding site or a redness is picked up or not based on the average value of the color tone feature value which the one target region group has.

29. A medical image processing method, comprising:
an image dividing step of dividing an image corresponding to a subject image which is picked up by a medical image pickup apparatus into a plurality of regions constituted of at least one or more pixels;
a feature value calculating step of calculating a color tone feature value which is a feature value based on a color tone of the image in each of the plurality of regions;
a first image region classifying step of classifying each of regions in which an image of a biological mucosa is picked up as the subject among the plurality of regions as a biological mucosa class;
a first color tone reference value calculating step of calculating a first color tone reference value based on the color tone feature value which each of the plurality of regions has;
a first lesion detection reference calculating step of properly calculating a first lesion detection reference for detecting at least either one of a bleeding site or a redness in accordance with the first color tone reference value;
a first image region detecting step of detecting a first target region that is a region in which an image of at least either one of a bleeding site or redness is picked up among the respective plurality of regions, based on the first lesion detection reference and the color tone feature value which each of the plurality of regions has;
a second image region classifying step of classifying a region in which a yellow color tone is remarkably shown as a yellow mucosal region, among each of the regions classified into the biological mucosa class, based on a classification result of the first image region classifying step;
a second color tone reference value calculating step of calculating a second color tone reference value based on the color tone feature value which each of the regions classified as the yellow mucosal region has;
a second lesion detection reference calculating step of calculating a second lesion detection reference in each of the regions classified as the yellow mucosal region in accordance with the second color tone reference value; and
a second image region detecting step of detecting a second target region which is a region in which an image of at least either one of a bleeding site or a redness is picked up, among each of the regions classified as the yellow mucosal region, based on the second lesion detection reference and the color tone feature value which each of the regions classified as the yellow mucosal region has.

30. The medical image processing method according to claim 29, wherein the first lesion detection reference calculating step properly calculates the first lesion detection reference based on predetermined table data relating to the first color tone reference value.

31. The medical image processing method according to claim 30, wherein the image dividing step divides the image into a plurality of rectangular regions having a predetermined number of pixels.

32. The medical image processing method according to claim 30, wherein the image dividing step divides the image by a pixel unit.

33. The medical image processing method according to claim 29, wherein the first lesion detection reference calculating step properly calculates the first lesion detection reference by using a predetermined function corresponding to the first color tone reference value.

34. The medical image processing method according to claim 33, wherein the image dividing step divides the image into a plurality of rectangular regions having a predetermined number of pixels.

35. The medical image processing method according to claim 33, wherein the image dividing step divides the image by a pixel unit.

36. The medical image processing method according to claim 29, wherein the first lesion detection reference calculating step properly calculates the first lesion detection reference based on a discriminator configured in correspondence with the first color tone reference value.

37. The medical image processing method according to claim 36, wherein the image dividing step divides the image into a plurality of rectangular regions having a predetermined number of pixels.

38. The medical image processing method according to claim 36, wherein the image dividing step divides the image by a pixel unit.

39. The medical image processing method according to claim 29, wherein the image dividing step divides the image into a plurality of rectangular regions having a predetermined number of pixels.

40. The medical image processing method according to claim 29, wherein the image dividing step divides the image by a pixel unit.

41. The medical image processing method according to claim 29, further comprising:

a target region extending step of setting one target region group by combining each of regions which is present in a vicinity of the first target region and has a color tone analogous to the color tone of the first target region among each of the regions classified as the biological mucosa class, to the first target region, based on the color tone feature value which the first target region has; and a target region determining step of determining whether the one target region group is a region group in which an image of at least either one of a bleeding site or a redness is picked up or not based on a number of regions which the one target region group has.

42. The medical image processing method according to claim 29, further comprising:

a target region extending step of setting one target region group by combining each of regions which is present in a vicinity of the first target region and has a color tone analogous to the color tone of the first target region among each of the regions classified as the biological mucosa class, to the first target region, based on the color tone feature value which the first target region has; and a target region determining step of determining whether the one target region group is a region group in which an image of at least either one of a bleeding site or a redness is picked up or not based on the average value of the color tone feature value which the one target region group has.

* * * * *